US010729874B2

(12) United States Patent
Zola et al.

(10) Patent No.: US 10,729,874 B2
(45) Date of Patent: Aug. 4, 2020

(54) SYSTEMS AND METHODS FOR TREATING MEMORY IMPAIRMENT

(71) Applicant: MapHabit, Inc., Atlanta, GA (US)

(72) Inventors: Stuart Zola, Decatur, GA (US); Matthew Golden, Decatur, GA (US)

(73) Assignee: MapHabit, Inc., Atlanta, GA (US)

( * ) Notice: Subject to any disclaimer, the term of this patent is extended or adjusted under 35 U.S.C. 154(b) by 0 days.

(21) Appl. No.: 16/525,486

(22) Filed: Jul. 29, 2019

(65) Prior Publication Data

US 2020/0030568 A1 Jan. 30, 2020

Related U.S. Application Data

(60) Provisional application No. 62/711,306, filed on Jul. 27, 2018.

(51) Int. Cl.
A61M 21/00 (2006.01)
G06F 16/55 (2019.01)
G06F 16/535 (2019.01)
G16H 50/20 (2018.01)
G16H 10/60 (2018.01)
G06F 3/0481 (2013.01)

(52) U.S. Cl.
CPC ........... A61M 21/00 (2013.01); G06F 3/0481 (2013.01); G06F 16/535 (2019.01); G06F 16/55 (2019.01); G16H 10/60 (2018.01); G16H 50/20 (2018.01); A61M 2021/005 (2013.01); A61M 2205/3303 (2013.01); A61M 2230/04 (2013.01); A61M 2230/205 (2013.01); A61M 2230/432 (2013.01); A61M 2230/63 (2013.01)

(58) Field of Classification Search
CPC ....... A61M 21/00; G16H 10/60; G16H 50/20; G06F 16/55
USPC ..................................... 600/26–28
See application file for complete search history.

(56) References Cited

U.S. PATENT DOCUMENTS

| 2002/0007105 | A1 | 1/2002 | Prabhu et al. |
| 2005/0228785 | A1 | 10/2005 | Wolcott et al. |
| 2008/0280276 | A1 | 11/2008 | Raber et al. |
| 2018/0024982 | A1 | 1/2018 | Fan et al. |
| 2018/0177973 | A1 | 6/2018 | Keene et al. |

FOREIGN PATENT DOCUMENTS

| CN | 103914794 A | 7/2014 |
| WO | 2015192189 A1 | 12/2015 |
| WO | 2018018925 A1 | 2/2018 |
| WO | 2018200641 A1 | 11/2018 |

(Continued)

OTHER PUBLICATIONS

International Search Report and Written Opinion dated Oct. 10, 2019 cited in Application No. PCT/US2019/043999, 11 pgs.

(Continued)

Primary Examiner — John P Lacyk
(74) Attorney, Agent, or Firm — Bekiares Eliezer LLP

(57) ABSTRACT

Disclosed herein are systems and methods for treating memory impairment, and more specifically to customized visual presentation for treating memory-related disorders and diseases. The disclosed systems and methods can predict clinical status of patients based on platform user behavior, such as those of patients. This abstract is intended as a scanning tool for purposes of searching in the particular art and is not intended to be limiting of the present invention.

20 Claims, 18 Drawing Sheets

(56) References Cited

FOREIGN PATENT DOCUMENTS

WO PCT/US2019/043999 7/2019

OTHER PUBLICATIONS

Kellogg et al., "Mind Mapping: Using Visual Thinking to Improve Patient Care and Quality of Life," JHR, Perspectives, Mind Mapping, Published online Oct. 20, 2017 at journalofhumanitiesinrehabilitation.org, 9 pgs.

Huba, "My Life as an Ongoing Cognitive and "Medical" Experiment, #MindMap," Hubaisms: Bloopers, Deleted, Director's Cut, 2012-2017, https://hubaisms.com/2016/01/05/my-life-as-an-ongoing-cognitive-and-medical-experiment, 12 pgs.

| Step # | Level of Impairment | Text | Picture | Video |
|---|---|---|---|---|
| 1 | H | Go to medication cabinet | <picture of cabinet> | |
| 2 | M | Grab pill bottle with white cap | <picture of pill bottle> | |
| 3 | L | Take out one white, round pill | <picture of round pill> | |
| 4 | M | Re-cap pill bottle (PB) | <picture capped PB> | |
| 5 | M | Replace PB on shelf | <picture of PB/shelf> | |
| 6 | M | Fill glass of water half full | <picture of glass of water> | |
| 7 | H | Put pill in mouth & feel on tongue | <picture of pill on tongue> | <video of action of putting pill in one's mouth> |
| 8 | L | Swallow Pill | <picture pill going into mouth> | |

*FIG. 3B*

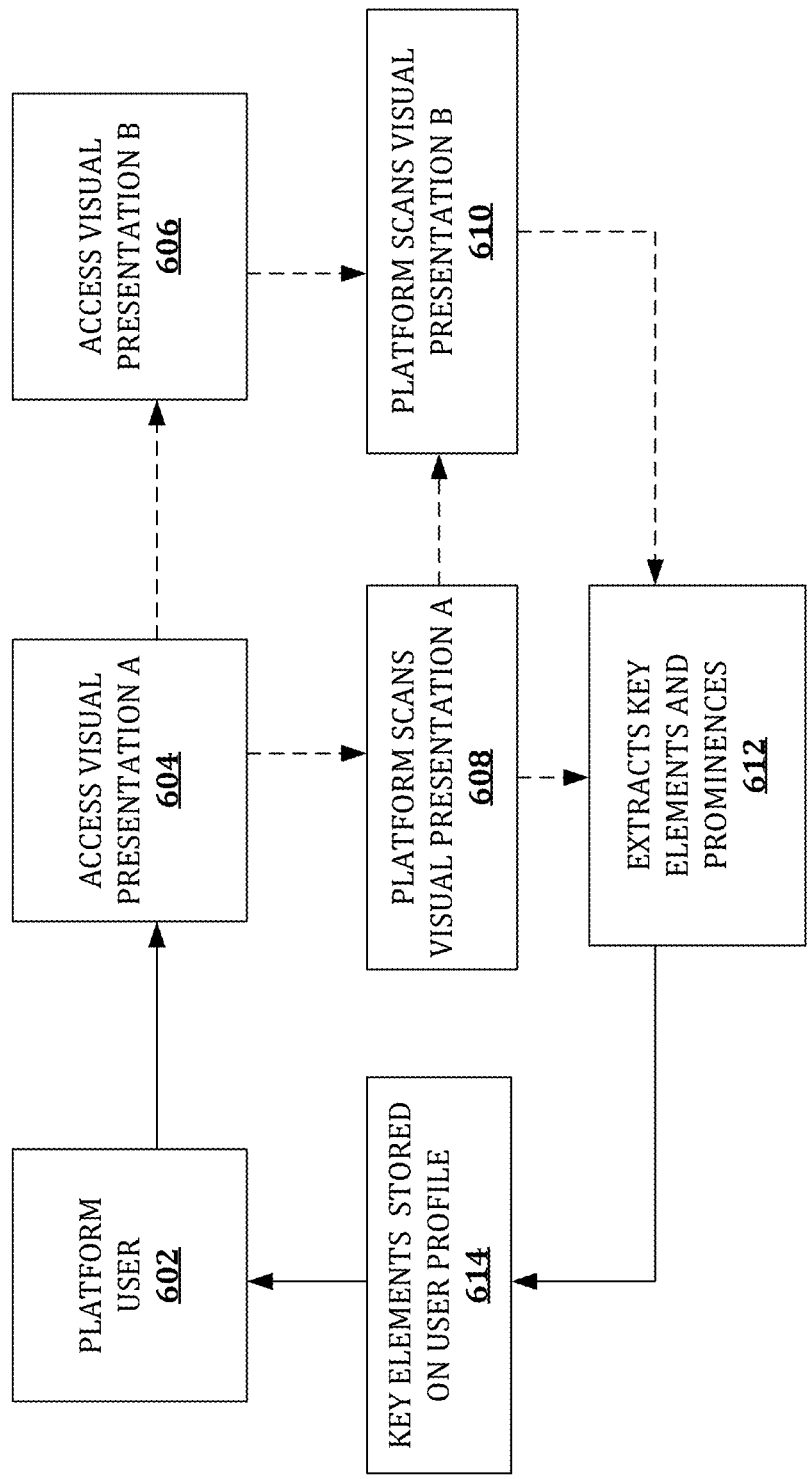

SYSTEMS AND METHODS FOR TREATING MEMORY IMPAIRMENT

CROSS REFERENCE TO RELATED APPLICATIONS

This application claims the benefit of priority to U.S. provisional application Ser. No. 62/711,306, filed Jul. 27, 2018, which is herein incorporated in its entirety. It is intended that the referenced application may be applicable to the concepts and embodiments disclosed herein, even if such concepts and embodiments are disclosed in the referenced applications with different limitations and configurations and described using different examples and terminology.

FIELD OF DISCLOSURE

The present disclosure generally relates to systems and methods for treating memory impairment, and more specifically to customized visual presentations for treating memory-related disorders and diseases.

BACKGROUND

Individuals with impaired memory and/or dementia, such as those with Alzheimer's Disease (AD) and related dementia (ADRD), can easily become stressed, frustrated, agitated, and often angry and withdrawn when they experience failures at tasks and activities of daily living (ADLs), especially ones that they previously could undertake and complete effortlessly. For those with dementia, the inability to perform ADLs increases risk of institutionalization and loss of independent living. For caregivers, this increases their levels of stress, depression, and physical burden.

The range of therapies available today to help individuals with AD/ADRD perform activities of daily living are severely limited. Currently available pharmaceutical treatments only provide modest improvements in cognition and are accompanied by significant side effects. Further, many current strategies for treating memory impairment rely heavily on bolstering dysfunctional regions of the memory system. However, these strategies for shoring up the dysfunctional regions of the memory system can only function in the context of the progressively deteriorating region and may be effective only for a relatively short time-course of progressive diseases. In the United States, AD/ADRD affects as many as 5 million people and nearly 40% of the population aged 85 and older. Approximately 13.2 million older Americans are projected to have AD/ADRD by 2050.

Accordingly, there remains a need for new systems and methods for treating memory impairment and memory-related diseases such as AD/ADRD. This need and other needs are satisfied by the various aspects of the present disclosure.

BRIEF OVERVIEW

This brief overview is provided to introduce a selection of concepts in a simplified form that are further described below in the Detailed Description. This brief overview is not intended to identify key features or essential features of the claimed subject matter. Nor is this brief overview intended to be used to limit the claimed subject matter's scope.

Both the foregoing brief overview and the following detailed description provide examples and are explanatory only. Accordingly, the foregoing brief overview and the following detailed description should not be considered to be restrictive. Further, features or variations may be provided in addition to those set forth herein. For example, embodiments may be directed to various feature combinations and sub-combinations described in the detailed description.

BRIEF DESCRIPTION OF THE DRAWINGS

The accompanying drawings, which are incorporated in and constitute a part of this disclosure, illustrate various embodiments of the present disclosure. The drawings contain representations of various trademarks and copyrights owned by the Applicants. In addition, the drawings can contain other marks owned by third parties and are being used for illustrative purposes only. All rights to various trademarks and copyrights represented herein, except those belonging to their respective owners, are vested in and the property of the Applicants. The Applicants retain and reserve all rights in their trademarks and copyrights included herein, and grant permission to reproduce the material only in connection with reproduction of the granted patent and for no other purpose.

Furthermore, the drawings can contain text or captions that can explain certain embodiments of the present disclosure. This text is included for illustrative, non-limiting, explanatory purposes of certain embodiments detailed in the present disclosure. In the drawings:

FIGS. 3A-3B illustrate customized visual presentations provided by the platform in accordance with exemplary embodiments of the present disclosure.

FIG. 6 illustrates an example of how the platform may track a patient's user activity in accordance with an exemplary embodiment the present disclosure.

DETAILED DESCRIPTION

Figure 1:
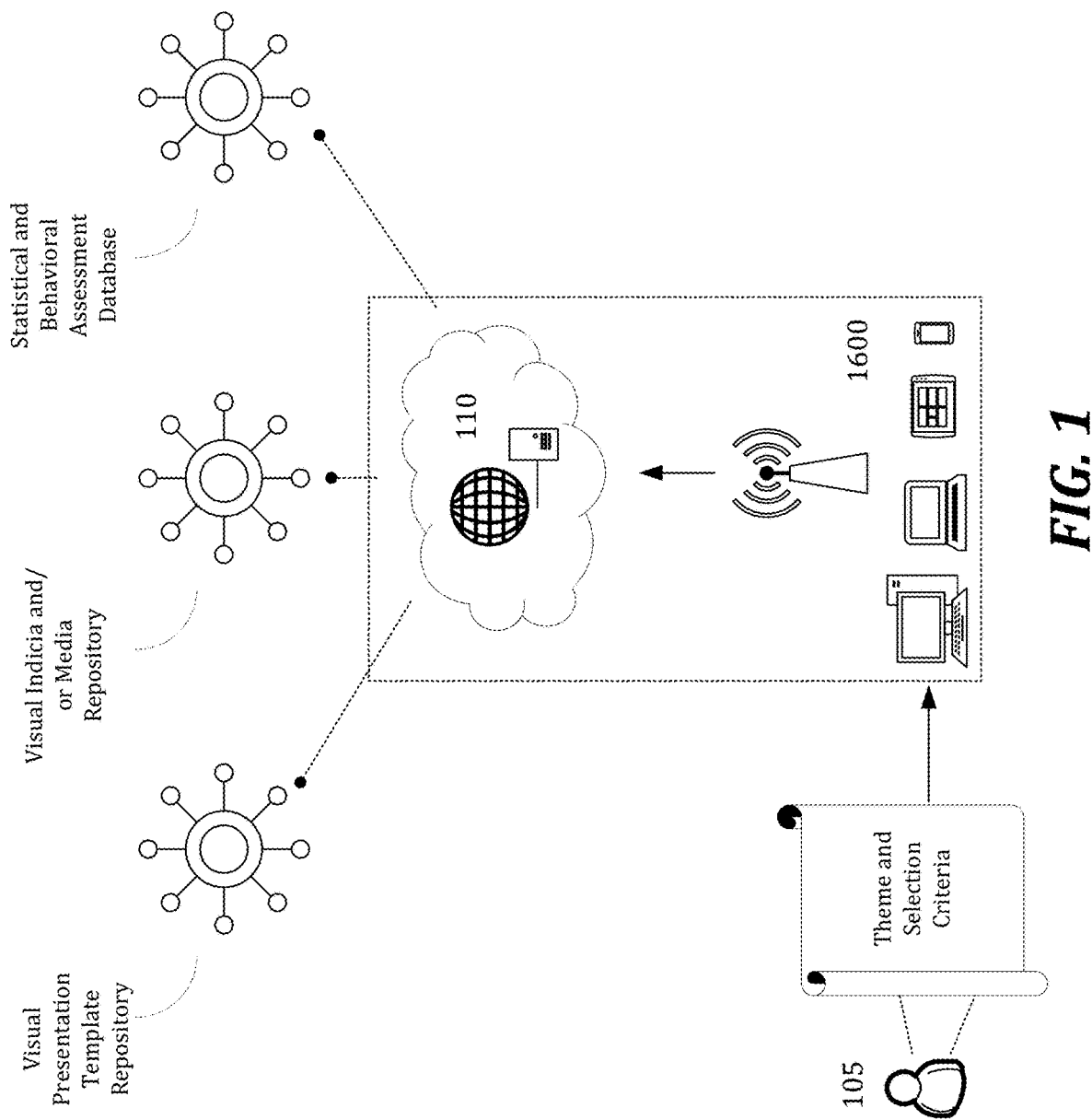
FIG. 1 illustrates a block diagram of an operating environment in accordance with an exemplary embodiment of the present disclosure.

As a preliminary matter, it will readily be understood by one having ordinary skill in the relevant art that the present disclosure has broad utility and application. As should be understood, any embodiment can incorporate only one or a plurality of the above-disclosed aspects of the disclosure and can further incorporate only one or a plurality of the above-disclosed features. Furthermore, any embodiment discussed and identified as being "preferred" is considered to be part of a best mode contemplated for carrying out the embodiments of the present disclosure. Other embodiments also can be discussed for additional illustrative purposes in providing a full and enabling disclosure. As should be understood, any embodiment can incorporate only one or a plurality of the above-disclosed aspects of the display and can further incorporate only one or a plurality of the above-disclosed features. Moreover, many embodiments, such as adaptations, variations, modifications, and equivalent arrangements, will be implicitly disclosed by the embodiments described herein and fall within the scope of the present disclosure.

Accordingly, while embodiments are described herein in detail in relation to one or more embodiments, it is to be understood that this disclosure is illustrative and exemplary of the present disclosure, and are made merely for the purposes of providing a full and enabling disclosure. The detailed disclosure herein of one or more embodiments is not intended, nor is to be construed, to limit the scope of patent protection afforded in any claim of a patent issuing here from, which scope is to be defined by the claims and the equivalents thereof. It is not intended that the scope of patent protection be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods can be shown and described as being in a sequence or temporal order, the steps of any such processes or methods are not limited to being carried out in any particular sequence or order, absent an indication otherwise. Indeed, the steps in such processes or methods generally can be carried out in various different sequences and orders while still falling within the scope of the present invention. Accordingly, it is intended that the scope of patent protection is to be defined by the issued claim(s) rather than the description set forth herein.

Additionally, it is important to note that each term used herein refers to that which an ordinary artisan would understand such term to mean based on the contextual use of such term herein. To the extent that the meaning of a term used herein—as understood by the ordinary artisan based on the contextual use of such term—differs in any way from any particular dictionary definition of such term, it is intended that the meaning of the term as understood by the ordinary artisan should prevail.

Regarding applicability of 35 U.S.C. § 112, ¶6, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. When used herein to join a list of items, "or" denotes "at least one of the items," but does not exclude a plurality of items of the list. Finally, when used herein to join a list of items, "and" denotes "all of the items of the list."

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component denotes the weight relationship between the element or component and any other elements or components in the article for which a part by weight is expressed. Thus, in a compound containing 2 parts by weight of component X and 5 parts by weight component Y, X and Y are present at a weight ratio of 2:5 and are present in such ratio regardless of whether additional components are contained in the compound.

As used herein, the terms "optional" or "optionally" means that the subsequently described event or circumstance can or cannot occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for treatment of one or more disorders prior to the administering step. In some aspects of the disclosed methods, the subject has been diagnosed with a need for treatment of one or more age-related disorder or disease prior to the administering step. In some aspects of the disclosed method, the subject has been diagnosed with a chronic pulmonary disease prior to the administering step. In some aspects of the disclosed method, the subject been diagnosed with a chronic pulmonary disease prior to the administering step.

As used herein, the term "treatment" or "treating" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed. For example, preventing memory-related disease or disorder means reducing the incidences, delaying or reversing diseases or disorders that are related to or associated with memory.

As used herein, the term "diagnosed" means having been subjected to a physical examination by a person of skill, for example, a physician, and found to have a condition that can be diagnosed or treated by the compounds, compositions, or methods disclosed herein. In some aspects of the disclosed methods, the subject has been diagnosed with a need for treatment of a memory-related disorder or disease prior to the administering step. As used herein, the phrase "identified to be in need of treatment for a disorder," or the like, refers to selection of a subject based upon need for treatment of the disorder. It is contemplated that the identification can, in one aspect, be performed by a person different from the person making the diagnosis. It is also contemplated, in a further aspect, that the administration can be performed by one who subsequently performed the administration.

As used herein, the term "providing" refers to any method of administering or dispensing treatment to a subject.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms but is generally insufficient to cause adverse side effects. The specific therapeutically effective level for any particular patient will depend upon a variety of factors including the disorder being treated and the severity of the disorder; the age, body weight, general health, sex and diet of the patient; the time of administration; the frequency of administration; the duration of the treatment. In further various aspects, a treatment can be administered in a "prophylactically effective amount"; that is, an amount effective for prevention of a disease or condition.

As used herein, the terms "memory-related disorder" or "memory-related disease" refers to disorders or diseases in which memory impairment is a major risk factor. In some aspects, memory-related diseases or disorders can be based on disease type, and can include, but are not limited to: degenerative diseases, including neuron degenerating disease (Alzheimer's, Parkinson's, Vascular dementia, Mixed dementia, Frontotemporal dementia, Huntington's disease, Chronic Traumatic Encephalopathy (CTE)); mental health disorders, including schizophrenia, mood disorders, including depression and anxiety; and function decreasing disorders or conditions, including declines due to age, or other so-called "benign changes with aging", e.g., poorer memory, cognitive decline, that have no specific neurodegenerative or biological bases. In other aspects, memory-related diseases or disorders can also be classified based on the type of cells or area of the brain involved, such as the hippocampus of the brain in Alzheimer's disease. In still other aspects, memory-related diseases or disorders can also be classified based on the type of cells or area of the brain spared from memory-related diseases or disorders, such as the neostriatum of the brain in Alzheimer's disease.

As used herein, the terms "page" or "screen" refers to a user screen or page within the platform displayed to a user for viewing and/or interacting with the platform. For example, an "attribute element screen" or "attribute element page" refers to a platform page or user screen corresponding to an attribute element within a visual presentation presented to a user, such as a patient, and contains content related to the attribute element.

The following detailed description refers to the accompanying drawings. Wherever possible, the same reference numbers are used in the drawings and the following description to refer to the same or similar elements. While many embodiments of the disclosure can be described, modifications, adaptations, and other implementations are possible. For example, substitutions, additions, or modifications can be made to the elements illustrated in the drawings, and the methods described herein can be modified by substituting, reordering, or adding stages to the disclosed methods. Accordingly, the following detailed description does not limit the disclosure. Instead, the proper scope of the disclosure is defined by the appended claims. The present disclosure contains headers. It should be understood that these headers are used as references and are not to be construed as limiting upon the subjected matter disclosed under the header.

The present disclosure provides various embodiments, features, and aspects that, individually or in various combinations, solve the problems presented by the current state of the art as described herein.

A. Platform Overview

Consistent with various embodiments and aspects of the present disclosure, provided herein are devices, systems, methods and/or techniques (hereinafter referred to as the "platform") for treating memory impairment using customized visual presentation of a theme, such as an event or activity. A platform consistent with embodiments of the present disclosure may be used by clinicians or health care organizations to determine, with relative accuracy, statistics about patients using the platform and groups of such patients. Such statistics may be used by the platform to predict, for example, but not limited to, a patient or group of patients' clinical status. The disclosure recognizes and addresses, in one aspect, the issue of presenting large amounts of information to individuals with impaired memory during visual-based treatment techniques. This overview is provided to introduce a selection of concepts in a simplified form that are further described below. This overview is not intended to identify key features or essential features of the claimed subject matter. Nor is this overview intended to be used to limit the claimed subject matter's scope.

In various aspects, the platform can be used by individuals (e.g., users, patients, etc.) who have dementia or other forms of memory impairment to overcome individual challenges of the activities of daily living. In further aspects, the platform can generate personalized visual presentations using visual presentation templates that will visually lay out the activities of daily life that will be encountered by these individuals who have dementia or other forms of memory impairment. Through the repeated use of the visual presentations of the platform, individuals with impaired memory can eventually develop habit routines through repeated consulting of the inventive visual presentations and maps. In still further aspects, the platform can maintain or bolster the habit regions of the patient brain (e.g., the striatum and the basal ganglia) through development and memory of routine habits, even in certain patients with Alzheimer's disease.

In further aspects, positive consequences of using the platform whereby memory-impaired patients continually have access to necessary information can include but are not limited to: reduced stress, confusion, frustration, and anger because they will not constantly worry about what they might be forgetting. Additionally, patients may become less dependent on caregivers and experience more autonomy, despite their medical condition. At the same time, the stress and burden experienced by caregivers may be significantly reduced, because patients may not be continually asking them the same questions repeatedly. Overall, relationships and communication between patients and caregivers may become more meaningful and productive.

In an exemplary aspect, the present disclosure provides a method to prepare or customize a visual presentation of a theme comprising: providing a parent visual element displaying information relating to a selected or designated theme, the parent visual element linked to or associated with at least one attribute visual element; providing at least one attribute visual element based at least on the selected theme, the at least one attribute visual element configured to be linked with the parent visual element in a linking pattern or arrangement; modifying the at least one attribute visual element to display visual indicia configured to communicate information relevant to at least one of: the parent visual element, the theme, determine a relationship between at least one of: the parent visual element and at least one attribute visual element, the at least one attribute visual element and the theme, and the at least one attribute visual element and another attribute visual element; generating based at least on a predefined visual presentation template, a visual presentation comprising the parent visual element linked with the modified at least one attribute visual element in a linking pattern or arrangement; displaying the visual presentation, the visual presentation configured for interaction with a subject or user.

In another exemplary aspect, the present disclosure also provides a system to prepare a visual presentation of a theme, comprising: at least one memory having computer-accessible instructions; and at least one processor function- ally coupled to the at least one memory and configured by at least a portion of the computer-accessible instructions: to provide a parent visual element displaying information relating to a selected or designated theme, the parent visual element linked to or associated with at least one attribute element; to provide at least one attribute element based at least on the selected theme, the at least one attribute element configured to be linked with the parent visual element in a linking pattern or arrangement; to modify the at least one attribute element to display content configured to communicate information relevant to at least one of: the parent visual element, the theme, determine a relationship between at least one of: the parent visual element and at least one attribute element, the at least one attribute element and the theme, and the at least one attribute element and another attribute element; to generate, based at least on a predefined visual presentation template, a visual presentation comprising the parent visual element linked with the modified at least one attribute element in a linking pattern or arrangement; to display the visual presentation, the visual presentation configured for interaction with a subject or user.

In another exemplary aspect, the present disclosure also provides computer-readable non-transitory storage medium comprising a set of instructions which when executed perform a disclosed method. In still another exemplary aspect, the present disclosure also provides devices and systems configured to execute one or more steps of the disclosed methods. In yet another exemplary aspect, the present disclosure also provides methods of treating a memory-related disorder using the disclosed systems and visual presentation templates comprising the step of administering a customized visual presentation to a subject, the visual presentation configured for interaction with the subject.

In another exemplary aspect, the present disclosure also provides methods and systems for dynamically adjusting or modifying the platform, such as visual presentations, based on user characteristics and behavior. In still another exemplary aspect, the present disclosure also provides methods and systems for determining, with relative accuracy, statistics about users interacting with the platform and groupings of such users. Such statistics may be used by the platform to predict, for example, but not limited to, a user's clinical status and develop models of trajectories through the illness. In some aspects, the user behavior data may be indicative of the clinical status of the user. In other aspects, data associated with user behavior may be used to help guide treatment choices for clinicians and permit time for families to prepare for upcoming changes.

Thus, in yet another exemplary aspect, the present disclosure also provides methods and systems for predicting clinical status of patients based on platform user behavior of patients. Embodiments of the present disclosure may operate in a plurality of different environments. For example, in a first aspect, the platform may receive notice that a patient has visited a visual presentation. Then, the platform may scan that page to gather raw data from the page. For example, the platform may use various algorithms, including, but not limited to, for example, machine learning techniques, natural language processing, and digital signal processing (audio/image/video data) to search the visual presentations for keywords or phrases. Still consistent with embodiments of the present disclosure, the platform may receive raw data as it tracks and/or monitors patient users throughout, for example, navigating and interacting with visual presentations. Tracking may include, for example, but not be limited to, scanning each visited user interface page or page in visual presentation so as to create a profile for the visual presentation. As will be further detailed below, the profile may be generated by, for example, the aforementioned algorithms used to gather raw data for the visual presentation.

Accordingly, in some embodiments, interaction of a user with the platform and a plurality of platform servers, such as for example, content servers, visual presentation servers and so on may be monitored. For instance, when the user views a visual presentation, a tracker or monitor may be initiated in order to save information regarding the user and/or the user's interaction with the visual presentation. For instance, the tracker may be initiated at the server side and may include information such as a timestamp corresponding to the user's viewing of the visual presentation and one or more identifiers associated with the user. The one or more identifiers may be for example, a network identifier such as a Platform protocol (IP) number and/or a MAC number, a device identifier such as an IMEI number, a software environment identifier, such as OS name, browser name etc., user identifiers such as email address, first name, last name, middle name, postal address etc. and values of contextual variables such as GPS location of the device used to access the visual presentation, sensor readings of the device or wearable device while accessing the visual presentation and so on.

In some embodiments, the one or more identifiers may uniquely identify the user while preserving anonymity of the user. In other embodiments, the one or more identifiers may be subjected to encryption in order to render the one or more identifiers unreadable to other users while maintaining the ability of the one or more identifiers to uniquely identify the user. For example, in some instances, tracker may be instantiated on a client side, where the tracker may reside on a user device, such as a tablet or a laptop computer. Accordingly, any information collected by the tracker may remain accessible in human readable form only within the user device. However, prior to transmitting the tracker to the server side, the information collected may be subjected to hashing. Accordingly, in some embodiments, information about the user in human readable form may not be available at the server side. Thus, users may be ensured of preserving their privacy.

In further aspects, embodiments of the platform may be used by clinicians or caretakers to determine the clinical status of and/or identify patient users of the platform who may be "in-need" of, for example, increased monitoring or clinical intervention with a calculated degree of confidence. Accordingly, targeted information, such as for example, patient user behavior and/or biometric data may be presented to such clinicians or caretakers in order to aid the clinician or caretaker to make informed patient care decisions while also enhancing the likelihood of the patient user's effective use and compliance with the platform. Although certain embodiments of the present disclosure may be disclosed with reference to a "clinician" or a "caretaker" as a platform user, any individual or entity may be a platform user.

In further aspects, the present disclosure provides methods of and systems for predicting a patient user as needing clinical intervention, based on collection and scoring (either statistically or using machine learning) of pieces of data extracted from user behavior data from interaction with the platform by a patient user. One possible user of the platform may be, for example, a clinician. A clinician may join or access a network having a plurality of patients (e.g. a patient-network) in order to collectively determine clinical status of patient users. The network may be associated with a plurality of tracking-enabled patient users. Accordingly, the present disclosure enables a clinician to determine if a patient user is 'in-need' for clinical services that the clinician provides. This is advantageous because if the patient is 'in-need', the clinician may reevaluate the patient, execute an appropriate intervention and/or adjust the personalized patient platform instance to increase the likelihood that the patient remains compliant and does not experience a worsen clinical status.

In some embodiments, a platform user may not be a clinician, but a caretaker or a family member. To this end, a platform user, such as family member or caretaker, may specify certain criteria for determining clinical or in-need status of a specific patient user without being required to join a network. As an example, regardless of whether the platform user is a caretaker or family member, the platform user may specify that it seeks to evaluate a specific patient on the platform. The platform may then, in turn, commence an analysis of platform behavioral data aggregated from only the specific patient's use of the platform.

Upon analysis, the platform may determine that the patient has visited a specific ADL visual presentation on multiple occasions. Accordingly, by tracking the patient's platform activity, the methods and systems disclosed herein may determine that the patient viewed 'Medication ADL' visual presentation five times and focused on an attribute element page corresponding to "pill". As detailed herein, such information may be extracted from the multiple data sources by the platform using a plurality of techniques. Such as, for example, but not limited to, using a tracker or monitor running on the patient device at the time the user visited them. Further, and as will be detailed below, key elements extracted from the accessed pages may be analyzed in order to determine whether the patient is in-need for one or more clinical interventions. In some embodiments, the disclosed methods and systems may also calculate a confidence score associated with the in-need status of the person with respect to the clinical intervention. For instance, the methods and systems disclosed herein may be able to determine that the patient is 73% in-need for increased monitoring, 59% in-need for adjustment of patient's visual presentation complexity or content, and 32% in-need for neuro-behavioral assessment.

Embodiments of the platform may further be used to enable a platform user (e.g., clinician, caretaker, or patient care facility) to better monitor its patients. Accordingly, data that has been acquired, aggregated, and processed by the platform may be provided to a platform user. For example, an application program interface (API) may provide statistics about single patients (e.g., likelihood that a patient's clinical status is worsening), or groups of patients (e.g., patients residing at nursing home and/or patients sharing a common diagnosis). Such statistics may be provided in, for example, lists, charts, and graphs. Further, searchable and sortable raw data may be provided. In some embodiments, the data may be provided to licensed users, such as authorized clinician within a healthcare organization. For instance, for patients that have identified data such as, advanced Alzheimer's Disease diagnosis, which has a list of known patients, clinicians may use the data to, for example, further monitor to their known list of patients or predict clinical status changes.

Both the foregoing overview and the following detailed description provide examples and are explanatory only. Accordingly, the foregoing overview and the following detailed description should not be considered to be restrictive. Further, features or variations can be provided in addition to those set forth herein. For example, embodiments can be directed to various feature combinations and sub-combinations described in the detailed description.

B. Platform Configuration

In one aspect, FIG. 1 illustrates one possible operating environment through which a platform in accordance with exemplary embodiments of the present disclosure can be provided. In further aspects, and by way of non-limiting example, a platform 100 can be hosted on a centralized server 110, such as, for example, a cloud computing service. The centralized server may communicate with other network entities, such as, for example, a plurality of host servers and a user device (e.g. laptop computer, smartphone, tablet computer, desktop computer, wearable device, smart speaker, etc.). Additionally, in some embodiments, the centralized server may also communicate with other entities such as databases, wearable devices, smart speakers, etc. In general, the centralized server may be configured to communicate with any entity capable of providing user behavior data or clinical data that is representative of a patient's clinical status. A user 105, which may be a patient ("patient user") or clinician ("clinician user") can access platform 100 through a software application. The software application can be embodied as, for example, but not be limited to, a website, a web application, a desktop application, and a mobile application compatible with a computing device 1600. One possible embodiment of the software application may be provided by the MapHabit System™ (MHS) suite of products and services provided by MapHabit™ Inc.

In various aspects, customized visual presentations of the platform can be based on a visual presentation template and/or historical information indicative of behavioral responses or user behavior data of one or more users (e.g., patients) during interaction with the platform, such as, for example, visual-based interaction of attribute elements within a visual presentation associated with a theme, such as steps in an activity or details of an event, and the like. Such interaction can pertain, for example, to checking steps in taking medication, preparing a recipe or recalling details of a planned outing to the movies. In further aspects, a parent visual element can display content such as visual indicia or information indicative of the theme, and an attribute visual element can display content such as visual indicia or information, such as textual data, indicative of attributes of the theme. In still further aspects, the historical information can comprise information indicative of a group of attribute visual elements respective to a theme. In yet further aspects, a visual element can be associated with content of the theme or attribute of the theme, thus historical information can include information indicative of user behavior associated with content related to the theme or attributes. To this end, historical information can permit generation of user behavior data, such as user interaction and/or viewing statistics— e.g., frequency of presentation of a visual element or content, viewing interval of a visual element or content, and the like, as described herein. In further aspects, at least a portion of the content associated with the visual elements may be generated by the platform based on the visual presentation template, selection criteria, and/or in response to user-based interaction or behavioral assessment of distinct users. In still further aspects, each of the attribute visual elements can include content comprising a plurality of media assets or visual indicia related to a specific attribute, where each of such media assets or visual indicia can correspond to certain aspects or traits of the attribute visual element.

In a further aspect, the platform can determine of one or more groups of prominent attribute elements of the theme. Each group of prominent attribute elements can have a prominence level. A prominence level may be associated with or correspond to a user condition, such as, for example, level of memory impairment. A prominent attribute element can be a visual element that is collectively preferred or otherwise recognized by users that utilize a visual presentation for a given theme. One or more groups of prominent attribute elements can be used to create a visual presentation template for a given theme and, in one aspect, to build customized visual presentation for users. Accordingly, several visual presentation templates can yield a plurality of customized visual presentations. For a specific group of visual presentation templates, various selection criteria can be utilized to identify the appropriate visual presentation template for user characteristics or theme.

In further aspects, various themes, which generally relate to an activity, event, or thing represented by a parent visual element and a plurality of attribute elements associated with attributes of the theme, may be available (e.g., persisted in the network repository or memory thereof) for user-based interaction or viewing activities, as described further herein. Visual elements can embody, comprise, display or otherwise present content such as visual indicia and/or a media asset. In some aspects, visual indicia can comprise at least one of alphanumerical characters, text, an object, shape, picture, symbol, icon, color, or the like, or combinations thereof. In other aspects, a media asset can comprise digital content (digital image(s) and/or video, digital audio, combinations thereof, etc.). In further aspects, the content may comprise content associated with one or more sensory modalities, including (but not limited to) vision, audition, and touch. In still further aspects, a sensory modality can comprise a sensory aspect of the content or type and location of the sensory receptor activated by the content. In yet further aspects, the content may comprise content associated with multiple sensory modalities. In some aspects, the content associated with multiple sensory modalities may be presented concurrently. Presentation of content associated with a parent or attribute element to a user may comprise a concurrent modality presentation (CMP) where one or more visual indicia and one or more media assets, or multiple media assets are concurrently presented to the user. For example, a concurrent modality presentation (CMP) may be where a static or action picture (i.e., a visual modality) is displayed to a user and, concurrently, voice-over audio (i.e., audition modality) describing the static or action picture is played to the user. Accordingly, the user sees the static or action picture while concurrently hearing the voice-over audio describing the picture. CMPs employed through the present platform can provide numerous advantages, including, but not limited to: aiding in habit memory formation, enhancing safety, enhancing personalization of visual presentations, and enhancing effects of reinforcement. CMPs may aid in habit memory formation by providing opportunity for redundancy of information and enhanced development of habit memory. For example, a medication visual presentation may comprise at least two CMPs (i.e., vision and audition) for every attribute element or step, and for some attribute elements or steps may have three CMPs (i.e., vision, audition, and touch). In some aspects, more modalities that can be brought to the user's attention or made available for interaction, the more effectively information is understood, recognized, and retained by the user. To this end, redundancy is understood to be established strategy for successful learning and retention. Further, CMP may enhance safety by providing a built-in check of accuracy and may reduce the possibility of error. For example, a medication visual template may show a picture of a large round pill and the concurrent audio describes the same features of the pill; but the pill the user has obtained from a pill bottle is square-shaped. A mismatch can signal to the user that the wrong pill has been selected, and the choice needs to be corrected. Still further, CMPs may enhance personalization of maps. For example, visual presentations may contain personalized content or information from family members in multiple modalities, including vision (i.e., pictures, videos, text notes) and audition (i.e., audio recordings). Using CMPs in a visual presentation for family personalization can enhance engagement by the memory impaired user, and content such as family messages can serve to encourage the user to engage in and complete activities. Yet further, CMP may enhance the effects of reinforcement. For individuals with memory problems, music in the form of favorite melodies, songs, or performers and/or pictures of scenes or people can often serve as reinforcing stimulus for sustaining habits. The effects of reinforcement can be strengthened further by presenting strong reinforcement stimuli concurrently in multiple modality presentations. For example, an ADL visual presentation for taking a shower may have imbedded in the sequence steps of attribute elements, a favorite melody or recording (e.g., Strangers in the Night) by a favorite singer (e.g., Frank Sinatra) whose picture is linked or associated with the music, and both stimuli linked to the specific step of turning on the shower. By way of further example, when steps for a shower have been completed, an "activity completed" may button appear on the user interface or device screen. The user sees the button, touches the button, hears a ding, followed by a short music interlude. To this end, the convergence of multiple modalities can serve as a strong reinforcement for having completed the sequence of steps and helps to ensure compliance on the subsequent interactions with the platform.

In various aspects, the platform provides methods and systems for determining, with relative accuracy, statistics about users interacting with the platform. In further aspects, each of the plurality of attribute visual elements provided in a visual presentation can be used for generation of various user statistics. For example, a customized visual presentation can comprise a plurality of attribute visual elements indexed or mapped in a linked pattern, and viewing and/or interaction statistics associated with such visual elements can comprise a histogram of interaction and/or viewing instances of visual elements. In further aspects, user behavior such as interaction and/or viewing instances of a visual presentation or visual element can be represented by a user interaction and/or viewing of the visual presentation and/or visual element within a predetermined range of interaction or viewing conditions. For example, certain user interaction and/or viewing instances associated with a visual presentation can be more frequent than others, conveying that certain content associated with the visual presentation may be less recognizable or memorable than others. In a further example, certain user interaction and/or viewing instances associated a visual presentation can be a longer duration than others, conveying that certain content associated with certain attribute elements may be less recognizable or memorable than others. In a still further example, certain user interaction and/or viewing instances of content associated with the attribute element can be more frequent than others, conveying that certain content associated with certain attribute elements may be less recognizable or memorable than others. In a yet further example, certain user interaction and/or viewing instances of content associated with the attribute element can be a longer duration than others, conveying that certain content associated with certain attribute elements may be less recognizable or memorable than others.

A prominent attribute element (or associated content) can be selected according to one or more selection criteria. In one aspect, a selection criterion can be "highest viewing interval." Thus, an attribute element or content associated with an attribute element that has the highest viewing interval can be selected as a prominent attribute or image from among a group of attribute elements or content. Selection of prominent attribute elements, such as evocative images, of a respective visual presentation or template can permit or facilitate dynamic adjustment and effectiveness of a visual presentation of the theme and understanding by the user. In some aspects, rather than supplying a large amount of information indicative of a large number of aspects or attribute elements representative of the theme—including unremarkable or ineffective attribute elements of the theme that are unlikely to be appreciated by a user or patient—the collective user preference for evocative or memorable visual elements or views, as suggested or evidenced by various measures of user behavior, can permit supplying a limited amount of information indicative of such prominent elements.

In further embodiments, the platform may be used by individuals or clinicians to determine, with relative accuracy, statistics about users interacting with the platform and groupings of such users. Such statistics may be used by the platform to predict, for example, but not limited to, a user's clinical status and develop models of trajectories through the illness. In some aspects, the user behavior data may be indicative of the clinical status of the user. In other aspects, data associated with user behavior may be used to help guide treatment choices for clinicians and permit time for families to prepare for upcoming changes. Primary outcomes measures in users may include variations in neurobehavioral status as demonstrated by functional measures and neuropsychiatric instruments, and relocation from independent living into a nursing home. In some aspects, primary outcomes measures may be chosen because they are generalizable and have high likelihood to significantly impact the life of individuals with AD/ADRD and their caregivers.

Accordingly, in further aspects, the platform may be configured to monitor user behavior and create a user profile indicating the clinical status of the user. In still further aspects, user behavior may include for example, platform activity performed by the user such as interaction with visual presentations, biometric data generated when interacting the platform, navigating through user interface screens of desktop application and/or a mobile application of the platform. The user behavior may include for example, data associated with present user interactions and/or historical user interactions with the platform.

In further aspects, the platform may receive a user behavior variable and threshold value associated with a patient list. The patient list may include a plurality of users associated with user behavior data corresponding to primary filtering criteria. The patient list may include user behavior variables and/or user identifiers of users who may have exhibited a certain user behavior in the past or are currently exhibiting such user behavior. For example, the clinician may specify the primary filtering criteria to be user viewing instance duration and corresponding threshold value (e.g. "time viewing an attribute visual element"; >2 minutes) in order to identify the patient list. Additionally, the clinician may reduce the size of the patient list by applying secondary filtering criteria, such as further specifying a theme (e.g. medication ADLs) or specific attribute element (e.g., medication ADL step—"take out pill" or "swallow"). Accordingly, a patient sub-population of users may be created based on analysis of user behavior data of users present in the patient list. In the present example, a user would have to have view at least one ADL step or user interface screen within a medication ADL visual presentation for longer than 2 minutes without advancing to the next step or user interface screen to be included in the patient sub-population listing. The patient sub-population list may present a set of users who may be more relevant to the clinician. Therefore, the clinician may specify a higher amount of monitoring to be used when administering medication to users in the patient sub-population.

In further aspects, the platform may gather biometric data from platform-connected wearable device worn by the user during interaction with the platform. Biometric data may include data associated with one or more of high-density accelerometry, actigraphy, quantitative and qualitative measures of sleep, average heart rate, and instantaneous beat-to-beat heart rate variability. Documented sleep disturbances and changes in sleep architecture in older adults has been reported to be associated with higher incidence of dementia over time. Further, instantaneous beat-to-beat variability have been shown to be an independent reflection of autonomic dysfunction as seen in Alzheimer's and Parkinson's disease. In various embodiments, and as detailed herein, the data may not be limited to platform generated data. For example, external clinical data, diagnostic data, medical history data, and many other data sources may be used.

In some embodiments, data derived from how users engage with the platform may divided into two or more categories, such as time series data and success rates. User behavior data variables measuring time series data may examine factors such as: viewing instance duration, duration required for the user to click through and/or navigate through user-interface screens, for example "time viewing a slide or text prompt prior to making a selection". In further aspects, the platform may capture data associated with physical measure of a user's interaction with their device within the platform, such as, and without limitation: strength of screen press, dwell time of finger on screen, navigation strategies, typing errors, and the like. In other embodiments, user data variables measuring success rates may include percentage of time where the user was assigned a task and successfully completed it. By way of non-limiting example, in a first aspect, the platform may notify or alert a user through a user interface or application interface to take a medication. Then, the platform may record and gather data from the user interface, such as, for example, whether the user was able to navigate through the user interface and mark the medication as taken. Changes in comprehension and executive function are expected to be expressed through how quickly a user is able to navigate through a visual presentation, and trend of changes correlate with clinical changes in the user's ability to function independently. Furthermore, biometric data from devices can also provide multiple additional indicators of user functional ability and/ clinical status.

The platform may use various algorithms, including, but not limited to, for example, machine learning techniques and digital signal processing (audio/image/video data) to search the user interface for key elements. Still consistent with embodiments of the present disclosure, the platform may receive raw data as it tracks users throughout, for example, the user interface screens and within customized visual presentations. Tracking may include, for example, but not be limited to, monitoring of each navigated screen or view so as to create a profile for the screen. As will be further detailed below, a profile may be generated by, for example, the aforementioned algorithms used to gather raw data for the user interface and visual presentation screens.

For instance, in some embodiments, where the user may access the same and/or different visual presentations through multiple user devices, a correlation of the information collected by multiple trackers may be performed in order to track the user. In some cases, each of the multiple trackers may not include all of the one or more identifiers. For example, the user may access a first visual presentation related to a first ADL using a smartphone, while the user may access a second visual presentation related to a second ADL using a tablet computer. In other aspects, the user may access a first visual presentation related to a first ADL using a smartphone, while in certain circumstances, the user may only access the first visual presentation using a smart speaker, such as when taking a shower.

Figure 9:
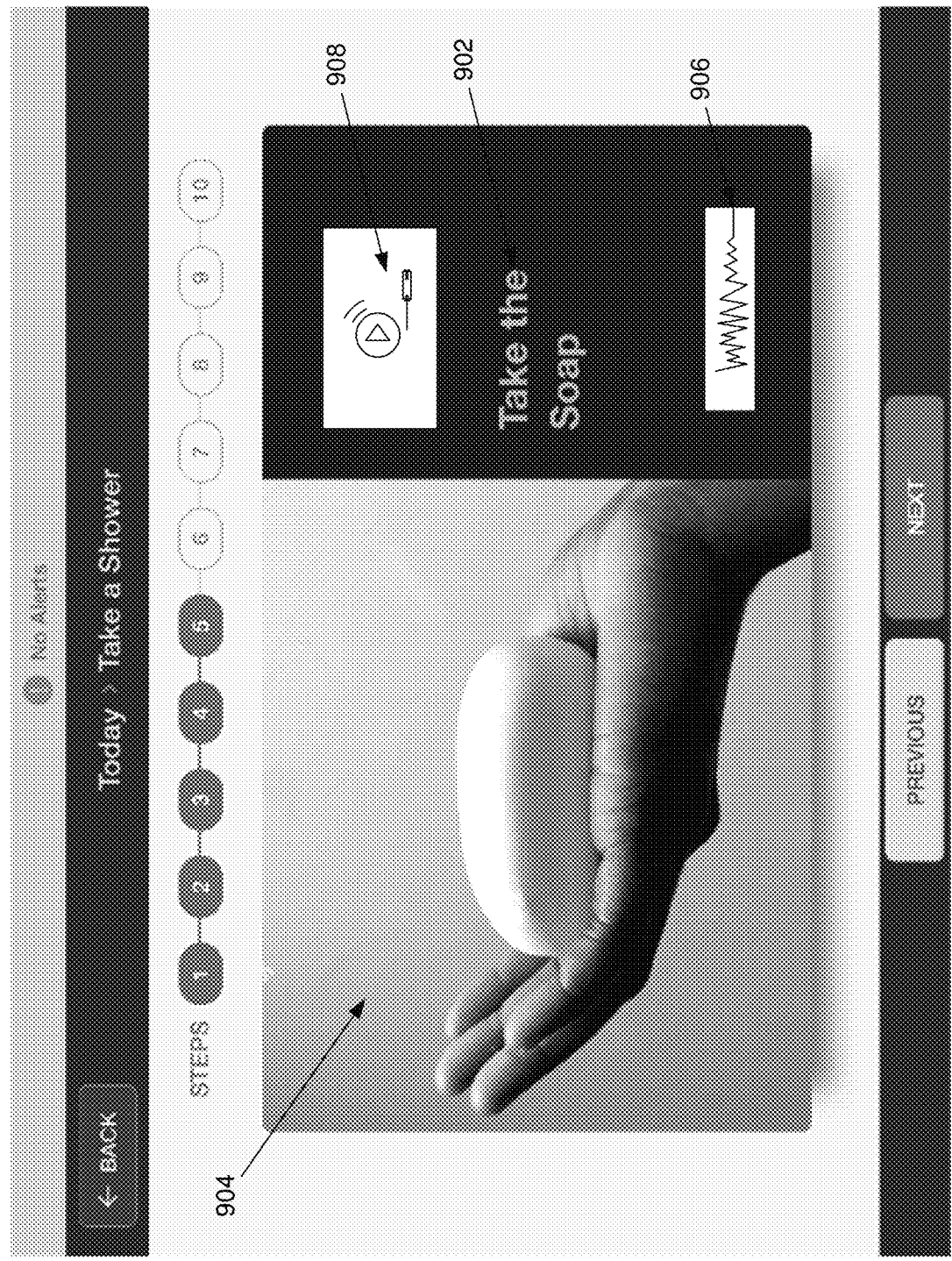
FIG. 9 illustrates a platform page 900 depicting a screenshot of a user interface screen corresponding to an attribute element from a visual presentation relating to taking a shower in accordance with an exemplary embodiment the present disclosure.

When scanning, the platform may perform, for example, natural language processing (NLP) to further process the context of the words and phrases in the text. In addition, the platform may utilize image recognition, audio recognition, and/or video recognition to gather data about the patient's platform use. FIG. 9 illustrates a platform page 900 depicting a screenshot of a user interface screen corresponding to an attribute element from a visual presentation relating to taking a shower. In various aspects, FIG. 9 shows how and where textual, image, video and audio information may be acquired to provide certain patient's platform use information. For example, text 902 may be scanned with optical character recognition (OCR). OCR scanning may generate words or phrases for characterizing the visual presentation. Text 902 from the visual presentation may also be extracted and analyzed using NLP. Further, image recognition software may be used to characterize the visual presentation. For example, artificial intelligence (AI) software may be used to determine whether image 904 is showing for example, a bar of soap. Image 904 may also be analyzed to characterize image characteristics such as flux, color, saturation, and the like. Audio content 906 from the visual presentation, or a related source, may also be scanned, using, for example, voice recognition software, to further provide information to further characterize the visual presentation. In further aspects, video content 908 may be converted to a series of images from periodic patient screens and scanned in the same manner as an image. In still further aspects, audio associated with the video content may be scanned to provide data about the visual presentation. Likewise, the combination of text, image, audio and video recognition may provide a humanistic view of what the visual presentation provides. The humanistic view may enable the platform to optimize characterization of the visual presentation.

In various further aspects, platform may receive general data. General data may include, for example, data from specific visual presentations (e.g., text, image, audio, and video data associated with the visual presentation) and data from individual users (e.g., visual presentation visited, information from the user's medical record, and the like).

In further aspects, platform may then analyze the gathered information associated with the patient's platform use. In some embodiments, the platform may perform natural language processing (NLP) as well as image, audio and video recognition to analyze the information. For example, the platform may use specific keywords and phrases, as well as keywords associated with image, video and audio files, found in visual presentation and attach a 'prominence' to an attribute element displayed on a page or screen. For example, for a visual presentation related to taking medication, the platform may return hundreds of 'keywords', including "pill" with high prominence, "glass of water" with medium prominence, and "cabinet" with low prominence. The platform may then interpret the information based on the patient's platform use to create a profile associated with the prominence of each attribute element within a visual presentation.

For example, a patient may continue or repeatedly access a number of attribute elements within visual presentations that have high prominence visual content and/or keywords associated with "pill". Such a patient may be statistically more likely to be having trouble remembering what their medication looks like. Such statistical predictions may be associated with a confidence level. Further, statistical predictions may be made for an abundance of other characteristics, such as, for example, but not limited to, age, clinical status, and disease state.

FIG. 6 illustrates an example 600 of how the platform may track an individual's platform use. The platform may track patient user 602 who may access multiple visual presentations such as visual presentation A and visual presentation B at different time instants, illustrated as steps 604 and 606 respectively. Accordingly, the platform may scan each of the visual presentations visited by the patient user 602, illustrated as steps 608 and 610. Accordingly, key elements such as content, keywords and corresponding prominence may be extracted based on analysis, such as NLP, illustrated as step 612. For example, content from a platform page, for example a user interface screen, such as textual and image content may be extracted. Further, non-textual content such as images, audio and video may be converted to textual content using one or more processes such as optical character recognition, speech recognition, image processing and so on. Subsequently, the textual content may be analyzed in order to identify the keywords and associated prominence which may then be stored in the user profile at step 614 and associated with the patient user. After platform analyzes the information for each patient, the method may proceed to a stage where platform may group users based on certain characteristics. For example, patients likely to be of a certain characteristic, such as, for example, gender, age, clinical status, and location (e.g., home vs. assisted care facility), may be grouped together. Additionally, patients may be grouped together based on selected preferences, such as, for example, treating physician or patient care location. Further, in some embodiments, the platform may be configured to predict a first part of a first profile corresponding to a first user based on a first part of the second profile corresponding to a second user. Additionally, the predicting may be based on a result of a comparison between a second part of the first profile and a second part of the second profile.

Accordingly, a profile of a user may further include one or more characteristics of the user, such as for example, a clinical characteristic such as level of memory impairment. Accordingly, in some embodiments, the first part may include one or more characteristics of the first user. Further, the second part may include at least one keyword and one or more corresponding prominence values. Accordingly, based on a match of keywords and prominence values of the first user and that of the second user, one or more characteristics, such as demographic characteristics, of the second user may be predicted based on the one or more characteristics of the first second user. In other words, based on a match of keywords and/or prominence values between two users, one or more characteristics of one user may be associated with the other user. Additionally, in some embodiments, the first part may include one or more keywords and one or more corresponding prominence values. Further, the second part may include one or more characteristics of the first user. Accordingly, based on a match of one or more characteristics of the first user and that of the second user, one more keywords and/or corresponding prominence values of the second user may be predicted based on one or more keywords and/or corresponding prominence values of first second user. In other words, based on a match of, for example, demographic characteristics between two users, keywords and/or corresponding prominence values of one user may be associated with the other user. Further, in some embodiments, a result of comparison of a keyword and a corresponding prominence value corresponding to each of the first user and the second user may be associated with a confidence value. Additionally, the predicting may be associated with an aggregated confidence value computed based on aggregating confidence values corresponding to each keyword and corresponding prominence value of a plurality of keywords and corresponding prominence values. For instance, each of User A and User B may be associated with a clinical characteristic such as a disease diagnosis. In some instances, each of User A and User B may each have a corresponding disease. Accordingly, User A may be identified as having Alzheimer's Disease (AD) while User B may be identified as having Parkinson's Disease (PD). Further, each of User A and User B are associated with a user profile including user behavior data and/or biometric data. User A may be associated with user behavior data influenced by Alzheimer's Disease, while User B may be associated with user behavior data influenced by Parkinson's Disease. Accordingly, each of User A and User B may be instances of the first user. Further, the first part of the profile associated with User A and User B may include the level of cognitive impairment. Furthermore, a User C may be an instance of the second user whose may not initially have been identified with a disease diagnosis. However, user behavior data, biometric data, and/or prominence values corresponding to the User C may be available. Accordingly, in an instance, user behavior data associated with the User C may be compared with user behavior data associated with each of User A and User B. A result of the comparison may indicate a greater degree of match between User C and User A. In other words, User C's user behavior may be more similar with that of User A than that of User B. Accordingly, it's more likely that User C may be associated with similar characteristics. Consequently, User C may be determined to have an Alzheimer's Disease diagnosis.

Similarly, in some instances, a characteristic of a user, such as disease diagnosis, may be predicted based on a match between user behavior data of the user and aggregated user behavior data of groups of other users with known information. For example, by aggregating user behavior data values of declared user characteristics, such as diagnosis or location, a first set of keywords may be identified that indicate neurobehavioral variables corresponding to clinical status predominantly influenced by the user characteristics. Accordingly, when a user with unknown disease state is encountered by the platform, keywords associated with the user may be compared with each of the first set of keywords and the second set of keywords. Further, based on a number of matches, the stage of disease progression of the user may be predicted. For example, if five of the most important keywords associated with the user are matched with the first set of keywords associated with a late stage while only two of the most important keywords matched with the second set of keywords associated with an early stage, the platform may predict the user to be at a late stage. In further aspects, key elements, keywords and user behavior data in the user profile may be associated with a confidence value in relation to the one or more user characteristics and clinical status being predicted. For instance, each keyword in a user's profile may be associated with confidence values in the form of a pair of numbers. For example, a keyword "pill" is associated with 50/50 indicating that the confidence with which "pill" indicates an AD diagnosis is identical to the confidence with which "pill" indicates a PD diagnosis. Similarly, instantaneous beat-to-beat heart rate variability may be shown to be associated with the confidence values 52/48 indicating that the confidence with which it indicates AD is not substantially greater than the confidence with which it indicates PD. Conversely, sleep disturbances may be shown to be associated with the confidence values 82/18 indicating that the confidence with which it indicates it indicates dementia is substantially greater than the confidence with which it indicates the absence of dementia.

In some embodiments, the confidence values may be derived based on statistical analysis of user behavior data variables and key elements such as keywords and/or corresponding prominence values of a large group of patients comprising both AD patients and PD patients. Further, in some embodiments, by aggregating user behavior data variables, key elements, keywords and/or prominence values across large groups of users, an accuracy of predicting clinical status and/or an unknown characteristic of a patient may be enhanced. Further, suitable mathematical functions may be applied to the group to balance against the keywords per person and mitigate skews. Subsequently, based on a comparison of the patient's keywords and/or prominences with that of the group's keywords and/or prominences, a prediction of the patient's clinical status may be determined with a higher confidence value. Using logic functions (e.g., AND, OR, and NOT), patients of a specific type may be grouped and sorted. Further, in some embodiments, patients may be aggregated using statistical functions such as, for example, weighted averages. Accordingly, a group profile corresponding to a plurality of users may be created. Further, the group profile may include a plurality of keywords and a corresponding plurality of group prominence values. A group prominence value of a keyword may be based on aggregation of prominence values of the keyword associated with the plurality of users. For instance, as shown, the plurality of users may correspond to a group of patients at a nursing home, and so on.

Further, each user may be associated with a user profile comprising keywords, corresponding prominence values and one or more other characteristics such as demographic characteristics. Additionally, in some embodiments, one or more of keywords, corresponding prominence values and demographic characteristics may be determined based on analysis of the visual presentations accessed and created by the users. By aggregating the prominence values for each theme across all users of the group, group prominence values may be obtained for each theme. As a result, user groups may be modeled with greater accuracy for reporting purposes.

In further aspects, the platform allows for adjusting platform characteristics, such as visual presentations and content, based on user characteristics and behavior. In still further aspects, the methods and systems allow for generating adaptive visual presentation that can dynamically adjusts based on user characteristics and behavior, such as degree of cognitive and/or memory impairment. In still further aspects, cognitive impairment can range from mild to severe, and the degree of impairment can affect a user's ability to comprehend and use the platform and effectively. As further described herein, degree of impairment may initially be determined independent of the platform. For example, an initial degree of impairment may be assessed by a standard of practice of administration and analysis of a battery of neuropsychological assessment tools. In various aspects, degree of impairment may be used by the platform to generate visual presentations that can be personalized. For example, the platform may use degree of impairment to determine at least one of: number of attribute visual elements or steps incorporated into visual presentations, increasing the size of text, reducing the complexity of content or images, pictures, and adding additional CMPs.

In further aspects, at least a portion of the visual elements can be personalized or modified by a user to display or present selected content. In some aspects, the user that is modifying the content may be the patient. In other aspects, the user that is modifying the content may not be the patient, such as a caretaker, family member, or clinician, or combinations thereof. In other aspects, modification associated with the methods and systems of the present invention can be based on user conditions such as level of severity or impairment of the users who are using the visual presentations, which, in some aspects, may be derived through use of the platform. Importantly, changes to the visual presentations can be modified as the user's level of impairment progresses, and may serve to enhance the ability of individuals with more severe impairments to continue engaging with the visual presentations effectively. A user with low level or mild impairment might require a visual presentation with only a few steps in order to successfully complete the ADL, whereas a more severely impaired individual might require that the ADL be presented and illustrated in many discrete, detailed steps for successful completion. By way of non-limiting example, in the early stages of Alzheimer's disease, when the individual is still fairly high-functioning, visual presentation with relatively complex features may be effectively used, such as those that have the upper limit of attributes or branches, smaller text, complex images, etc.

Prior visual methods and systems use a large number of features to enable individuals to do very complex things in creating their visual maps. These include, for example, having available the choice of large numbers of varieties of fonts, of graphics, of links to multiple web sites, and of the number and complexity of branches that can be generated within a single map. While complexity of features may be desirable in certain applications and uses, it is believed to be counter-productive for the present purposes. In some aspects, for individuals with impaired memory and progressive neurodegenerative diseases like Alzheimer's disease, an abundance of choices and information, can contribute to their current state of stress and confusion. Instead, having visual presentations and maps with fewer options and less information to process, may benefit them. Further, visual presentations of the present platform, which are easy to create and have relatively simple steps to follow or information to impart, are necessary conditions for them to be effective in helping the user to develop the habit routine, such as those described herein.

Again, as the disease progresses, the user may become less likely to effectively utilize a baseline or low impairment level visual presentation. Instead, one or more visual presentation features will need to be modified, adjusted or personalized for the user, such as reduced numbers of attributes or branches, reduced numbers of text words, reduced image complexity, increased font size, and/or larger images as part of the personalization process. In further aspect, additional means of modification or personalization of the visual presentations may include incorporating personal information. For example, the visual presentations may be personalized by incorporating user-specific or personal information, such as content (music, voice, stories) associated with the memory-impaired user's family, as well content such as pictures of the environment where the user resides. Incorporation of user-specific or personally-relevant content or components into the visual presentations serves to enhance memory, as well as compliance because the use of these components can increase engagement with the visual presentations and ensure continued development of the habit.

In further aspects, the visual presentations may be adjusted for different levels of technical ability. For example, the visual presentations may be personalized in terms of level of technical expertise, ranging from full-on use of smart devices, wearables, and voice-activated assistants (e.g., Alexa from Amazon), to low-tech kits that utilize paper printouts of visual presentations and magnetic boards that can illustrate the steps of specific visual presentations. In still further aspects, printouts and the magnetic boards can be mounted in specific locations of the user's residence (e.g., bathroom, bedroom, kitchen) adjacent to where the user will carry out the specific ADLs. Close contingency between the behavior to be carried out and the stimulus that signals the habit (whether a smart device, paper map, or magnetic board) enhances the ability of the individual to engage the behavioral habit and the habit region of the brain. In still further aspects, the visual presentations may be adjusted for different living environments. For example, visual presentations may be personalized in terms of the user's residence environment, which may vary from personal residence to institutional facilities. In some aspects, ADL visual presentations may utilize content in the form of real-time pictures of actual places (e.g., bathroom shower) and things (e.g., pill bottles) where the user currently resides. As a user's situation changes or the user moves to a different residence or environment, visual presentations can easily be adjusted to reflect the new details or attributes associated with the new environment while the ADL theme of the visual presentations remain consistently the same. Further, the ability to maintain consistency in the general attribute elements of the ADL habit behavior (e.g., the shower is still in the bathroom) can lead to better engagement and less disruption from minor changes related to the specific content associated with the attribute element (e.g., pill bottles are now on the shelf, not in the medicine chest). Still further, maintaining routine behavior can be a key component of successful habit building and memory enhancement.

In various embodiments, the platform can work with virtual assistants, such as Alexa from Amazon, and/or voice-enabled "smart speakers", such as Amazon Echo. The platform may work in conjunction with Alexa as a "skill" or add-on functionality. To this end, and by way of non-limiting example, the user can press an activation button and/or say an activation phrase "Alexa, open MapHabit" to activate and otherwise access the add-on functionality of the platform. Since the platform may use private data and/or confidential information; the user may be prompted to do a validation check. In this case, the user may provide a password or other form of authentication. In further aspects, the platform may work in conjunction with additional voice-enabled products such as SIRI, Google Assistant, and the like. The user may then be prompted to make a request, in which the user could respond with a command or say "settings" to edit the settings for the platform or language used by the platform. In some aspects, some or all of the content may be presented to the user through the smart speaker. In other aspects, some of the content may be presented to the user through the smart speaker and some of the content may be presented to the user using another smart device, such as mobile device, or using paper-based media, such as print-outs. For example, in a concurrent modality presentation (CMP), a static or action picture (i.e., a visual modality) may be displayed to a user using a mobile device or print-outs while concurrently playing voice-over audio describing the static or action picture using a smart speaker.

In further aspects, the platform may be accessed via various other internet-connected devices. To this end, the platform may comprise functionality that allows the highly personalized visual presentations to be accessed through the various other internet-connected devices, and allows interoperability between a user's mobile device and other technology platform, including internet-connected devices, or smart devices, to bring medical care into the home. For example, the platform may be activated by voice or by a wearable worn discretely on the body, which can minimize cognitive and physical barriers to using the platform. In further aspects, the platform can comprise of a plurality of repositories or databases. In yet further aspects, the database can comprise an image repository, or visual presentation template repository, or a customized visual presentation repository for users, or a combination thereof. In still further aspects, the platform can comprise at least one data received from the database or repository. In even further aspects, the data can comprise a plurality of images or templates. In other aspects, the templates can comprise a theme related to a category, topic, types, or a combination thereof. In further aspects, the platform can analyze the indicia on attribute visual elements to identify one or more keywords. In still further aspects, the keywords can be used in selecting images or media assets in preparing customized visual presentations.

In other embodiments, a non-patient, clinician user, such as a healthcare professional or clinical manager of a healthcare organization may also access platform 100 through a software application. The user may provide input parameters to the platform. Input parameters may be certain device IDs, patients living in a specific nursing home location with a nursing, indication of a list of visual presentations, indication of one or more attribute elements contained within a visual presentation from the list of visual presentation, indication of a list of record events signaling loss of independence, and indication of one or more interventions to be targeted to patient identified as meeting a predetermined clinical level (which may be referred to here as in-need patients). In response, the platform may identify in-need patients based on platform behavior and enable the clinician user to view in-need patients along with confidence values associated therewith.

In order to determine the clinical status of patients, the platform may be configured to track platform activity of patient using the platform. For instance, in some embodiments, the platform may be configured to use client-side or server-side user activity monitors or trackers in order to track a patient user across a plurality of attribute element pages from various visual presentations. Accordingly, a tracker stored in the patient device may be used to monitor and/or log each attribute element page of the plurality of attribute element pages from a visual presentation accessed by the patient device. The platform may extract user behavior data while creating a log of the patient device, represented by a unique ID, such as for example, a network address, an IMEI number, a combination of software, hardware and demographic information associated with a person operating the patient device and so on.

As a result of the tracking, for each unique ID representing a patient, a list of customized visual presentations may be identified for that patient. The platform may then access and scan attribute element pages from within the list of visual presentations in order to retrieve key elements present in the content of each visual presentations. For example, the platform may perform scanning, scraping, OCR, etc. in order to parse the content of each page. Further, the key elements may be aggregated and an analysis may be performed on the aggregated key elements in order to determine clinical status and/or identify in-need status of the patient for potential clinical intervention. Key elements may be analyzed based on a set of criteria in order to determine the corresponding patient's in-need status. For example, the platform may be configured to assess various factors associated with the key elements, including, but not limited to, keywords, keyword density (e.g., frequency of occurrence in a visual presentation), themes associated with the page and/or visual presentation, user behavior data such as time spent on a page and/or visual presentation, quantity of pages visited with related key elements, and parameters associated therewith. The analysis may be embodied using, at least in part, various machine learning methods and techniques. In turn, the analysis may also identify a confidence value associated with a clinical status and/or need for clinical intervention to which the in-need patient status corresponds.

In some embodiments, platform behavioral data may be combined with electronic medical record (EMR) data, retrieved from an EMR database, and biometric data, retrieved from wearables, and the like. The combination may then be used to identify patterns of user activity representing clinical status, such as level of memory impairment. Such patterns may be identified by performing machine learning over the historical user behavior data. Subsequently, the machine learning may be used to identify in-need status of the patient based on currently received user behavior data.

Figure 10:
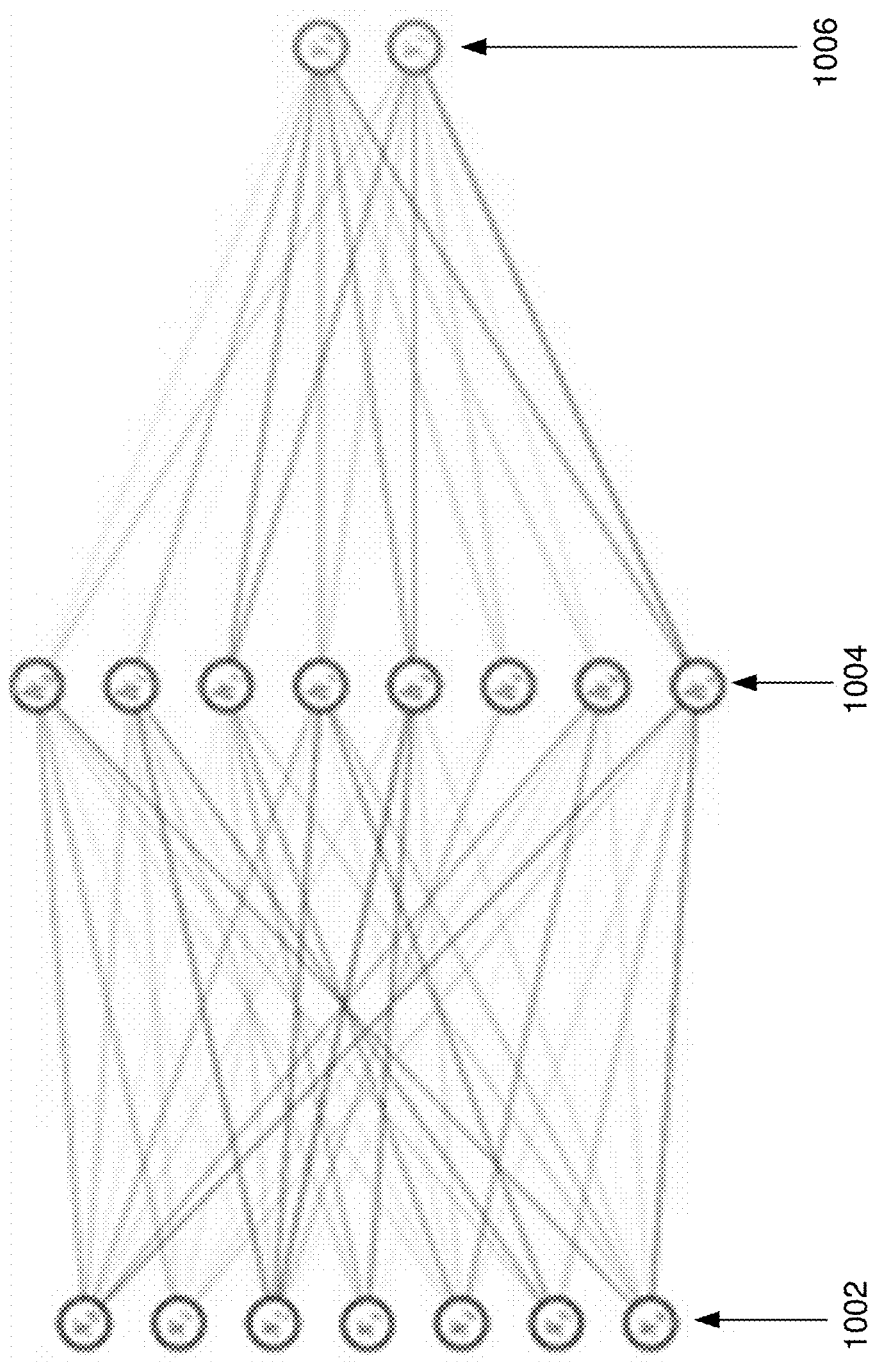
FIG. 10 illustrates a neural network model for predicting and identifying future clinical outcomes in accordance with an exemplary embodiment the present disclosure.

In other embodiments, the platform may construct a prediction model that may determine clinical status and/or identify future clinical outcomes of patients. In further aspects, the prediction model may comprise a feedforward artificial neural network with back propagation such as the shown in FIG. 10. Nodes may be arranged as an input layer 1002, a hidden layer 1004, and output layer 1006. Input layer may contain user behavior data and/or biometric data and/or user characteristic information. Output layer may contain various neuro-behavioral measurements and various loss of independent function outcomes. In further aspects, variables in the input and output layer may be separated by a constant time-interval to ensure consistency. In still further aspects, users may be randomly divided into a training and cross-validation groups (70%), and a validation group (30%). K-fold cross-validation during training and the internal validation group may help prevent overfitting of the data and ensures internal validity. As will be detailed with reference to FIG. 13 below, the computing device through which the platform can be accessed can comprise, but not be limited to, for example, a desktop computer, laptop, a tablet, or mobile telecommunications device.

C. Platform Operation

According to various aspects of the present disclosure, provided herein are devices, systems, methods, and techniques for treating memory impairment (collectively referred to as the "platform"). According to further aspects, the platform uses customized visual presentations for treating memory impairment. In still further aspects, the platform can be comprised of various disclosed methods and systems implemented by a computing device. As will be detailed below with respect to FIG. 13, the computing device (e.g., computing device 1600) can comprise various computing modules having software instructions for performing and operating at least a portion of the various disclosed methods and techniques. Furthermore, in some embodiments, different operations may be performed by different networked elements in operative communication with computing device 1600. For example, a server may be employed in the performance of some or all of the stages in the disclosed methods. Moreover, the server may be configured much like computing device 1600.

In one aspect, an initial user interface (UI) can be provided by the platform. The initial UI can be used as an interface for the platform to gather user profile data, such as user characteristics and demographics, selected theme and selection criteria for generating a customized visual presentation. The UI can comprise various input fields and buttons to enable the user to provide such data and make choices to guide underlying calculations and/or generation of personalized visual presentations.

Figure 2:
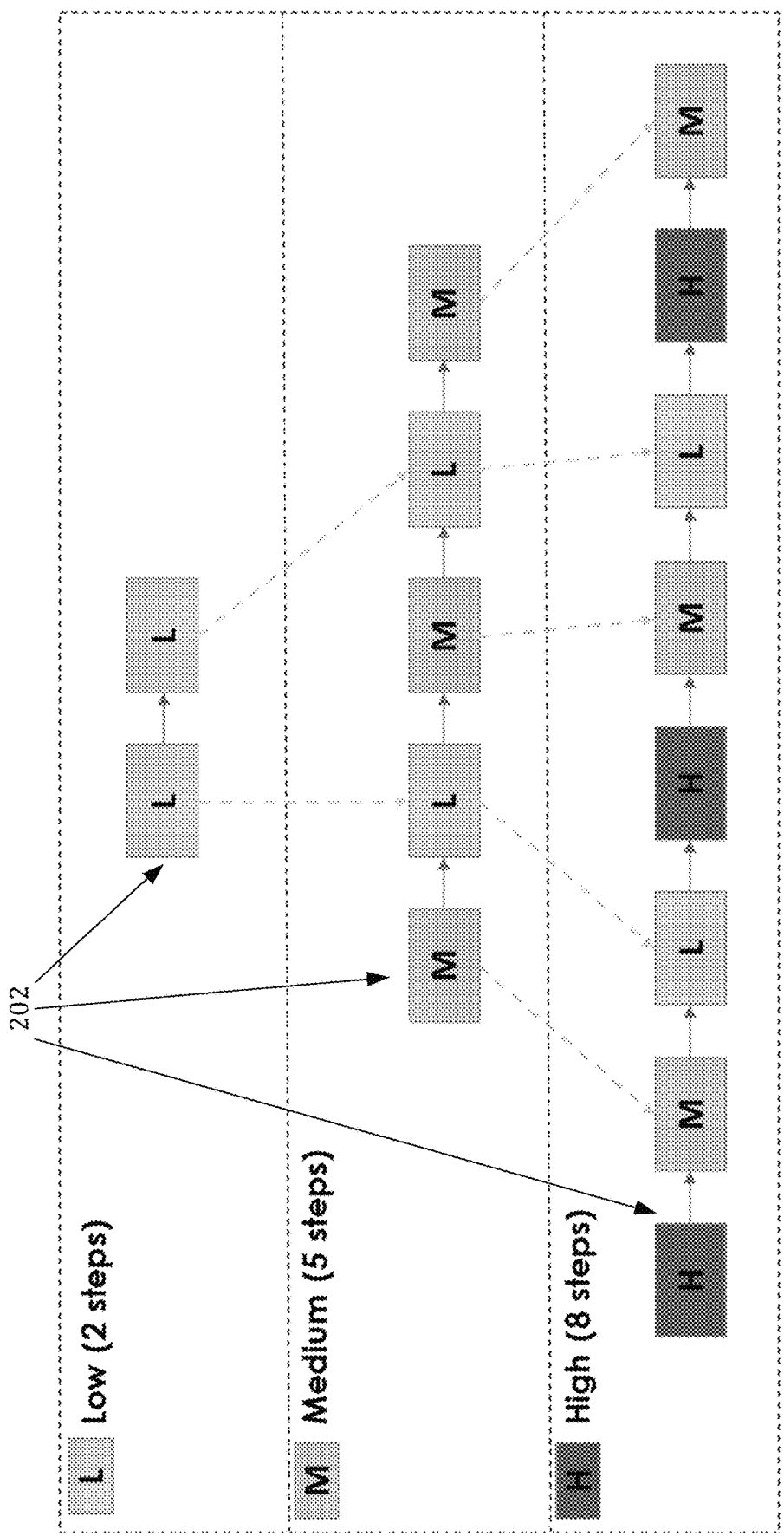
FIG. 2 illustrates a visual presentation template provided by the platform in accordance with exemplary embodiments of the present disclosure.
Figure 3A:
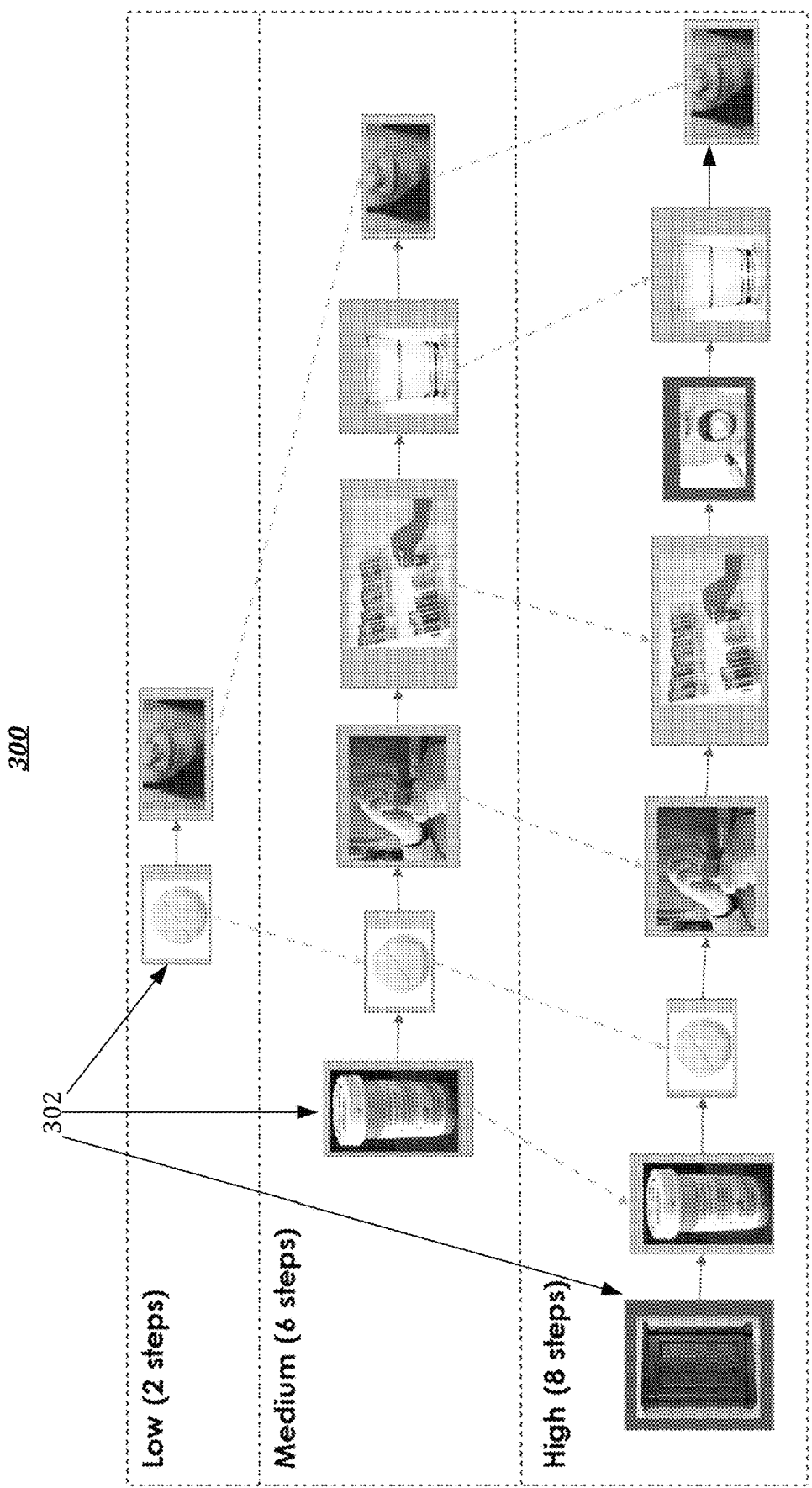

These data can also be used by the platform in generating and composing customized visual presentation comprising visual element branches, as described herein, the products of which can be used to treat memory impairment, for example, dementia. Still consistent with embodiments of the present disclosure, the platform can generate customized visual presentation in the form of visually branched visual elements for a designated theme. FIGS. 2, 3A-3B illustrate various example visual elements of customization of visual presentations of a theme in accordance with one or more aspects of the disclosure.

Figure 13:
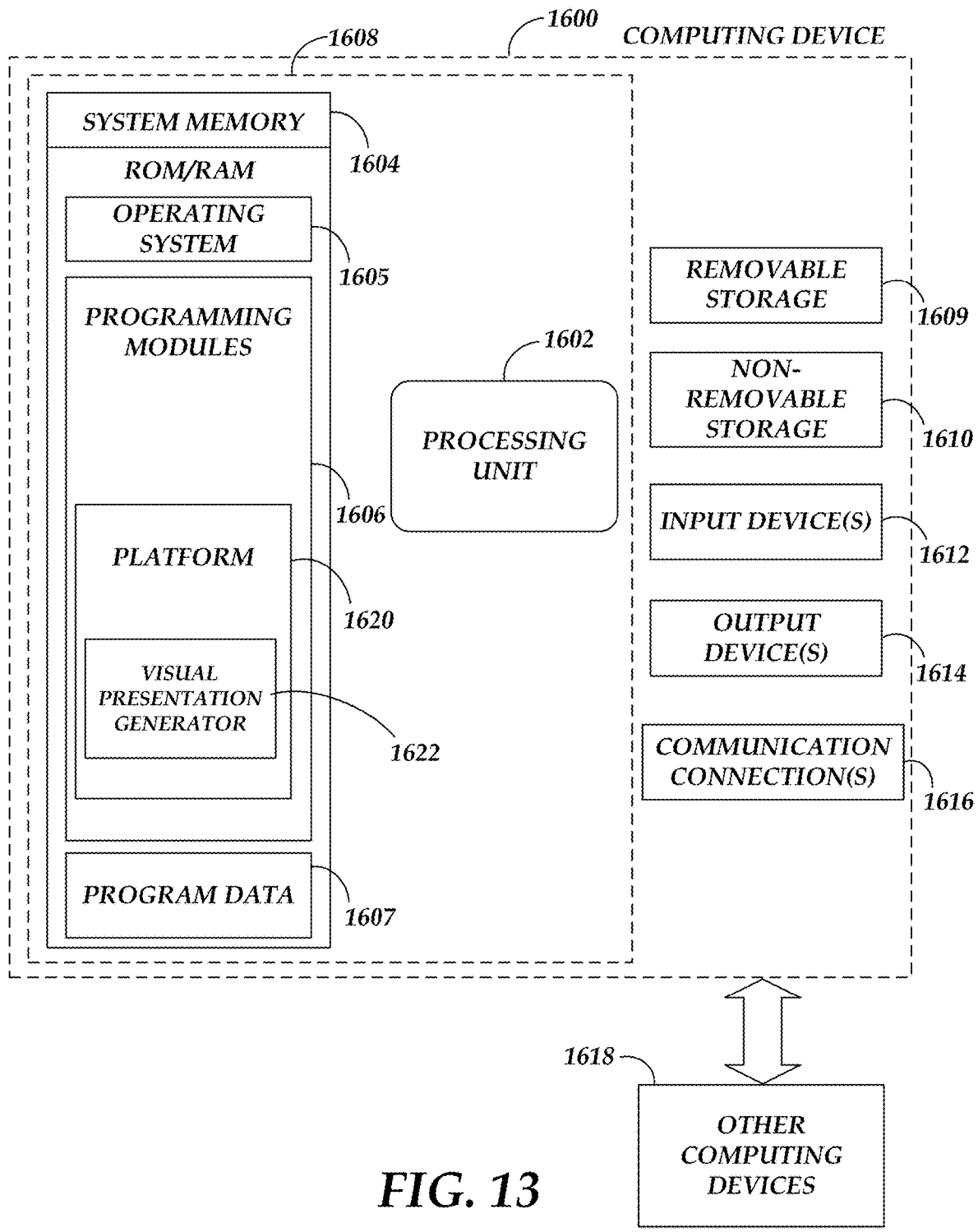
FIG. 13 illustrates a block diagram of a computing device consistent with exemplary embodiments of the present disclosure.

Consistent with embodiments of the disclosure, the platform can include a visual presentation generation module or component. The visual presentation generation module 1622 (FIG. 13) can be enabled to generate customized visual presentations. As illustrated in FIG. 13, the visual presentation generation module 1622 can be a module contained within the platform 1620. In other embodiments, the visual presentation generation module 1622 can be independent of the platform 1620. In various aspects, a visual presentation according to the present invention can comprise personalized or customized visual map containing layout and styles used to configure content such as visual indicia and images that can enhance the processing of information and memory function in memory-impaired individuals, including those with dementia. In further aspects, the theme of the customized visual presentation can focus on single components of an individual's activities of daily living (ADL) and/or instrumental activities of daily living (IADL). In yet further aspects, the customized visual presentations can be based on user characteristics, including at least one of: cognition level; degree of cognitive impairment, level of memory impairment, age, sex, nationality, spoken language, disease progression, and the like. To this end, an individual recently diagnosed with AD/ADRD (early stage) benefits from assistive technologies differently than an individual whose condition has progressed to severe impairment (late stage)

requiring assistance with basic activities. Thus, visual presentations can be adjusted by the platform to match the needs of users with a wide range of cognitive impairments, including but not limited to: adjusting the number of attributes or branches associated with a single visual presentation, adjusting font size used, adjusting amount of text on each attribute or branch, adjusting colors and contrast, adjusting complexity of symbols, adjusting image visibility (e.g., a visual angle in the range of from about 15 to about 65 degrees, including exemplary values of 20, 25, 30, 35, 40, 45, 50, 55, and 60), adjusting focus or prominence of attributes within a visual presentation or theme, and adjusting visual presentation complexity. In further aspects, the visual presentation may comprise a baseline or template presentation with a predetermined set of levels for severity of impairment and/or stage of medical condition that the individual is experiencing. For example, a visual presentation may include three levels of complexity that can be toggled to make them suitable for mild, moderate, or severe levels of memory impairment in individual patients.

As described herein, personalized or customized visual presentation can be based on a presentation template and/or user characteristics. In some aspects, a presentation template can have from about 2 to about 10 attribute branches or steps, such as, for example, from about 5 to 7 or 7 to 9 branches or steps. In still further aspects, a present template may have from 1 to 10 levels, corresponding to a user characteristic, such as level of impairment. By way of non-limiting example, a presentation template may be directed to a particular activity type, such as a patient's appointment with a physician. In further aspects, the presentation template for that particular activity may have several attribute elements or branches that provide information related to the theme or activity. A presentation template may be retrieved from a presentation template repository or database, and may be presented to the user according to one or more selection criteria provided by the user. For example, selection criteria may be "event" for theme and "Movie Night" as event type, and thus, one or more presentation templates matching the selection criteria may be provided to the user.

In yet further aspects, attribute elements can include one or more of each of the six "Ws": "What", "Who", "Why", "When", "Where", and "What Else". In a specific example, attribute element can be branches that include: Branch 1: ("What")—Doctor's appointment; Branch 2: ("Who")—Doctor's name; assistant or receptionist's name; who will go with me; Branch 3: ("Why")—Purpose of visit; first visit? checkup? medication evaluation? Will there be lab tests; Branch 4: ("When")—Date and time of appointment; alarm reminders; Branch 5: ("Where")—Location of doctor's office; directions for driving, or for public transportation; parking information, including fees; instructions for using transportation methods; and Branch 6: ("What Else")—Do I bring medications? list of questions since previous visit; discuss side effects or unusual symptoms; other supporting material for visit. In some aspects, a non-patient platform user, such as a caregiver, can modify or add content to the presentation template, for and/or in addition to the patient. In other aspects, the non-patient user may modify or add content together with the patient. In further aspects, the presentation template can facilitate a medical visit and facilitate interaction that the medical practitioner will have with the patient because many of the questions or concerns will already be in place on the customized visual presentation generated from the template and the patients can be reminded of those simply by accessing their customized visual presentation. While the customized visual presentation may be initially generated or accessed through a mobile device or computer, a printed version of the customized visual presentation can be made so that the patient can carry it to the appointment, or otherwise have it available for review and memory training.

In an exemplary embodiment, FIG. 2 shows a visual presentation template 200 and components in the form of attribute elements 202 for generating a customized visual presentation in accordance with the platform. As shown, attribute elements 202 have an arrangement in the presentation template with 3 levels, corresponding to 3 level of impairment, low, medium, and high. Each of the template levels contain 2, 5, or 8 attribute elements, presented as steps in a sequence in this template. During a creation or set-up phase, all of the plurality of attribute elements 202 may be present at once in the arrangement for the user to modify each attribute element to reflect personalized information and details. Alternatively, each attribute visual element may be individually presented to the user to modify or provide the relevant content or details, and a personalized visual presentation is generated or composed upon providing all the necessary information for each attribute visual element. In some aspects, the platform may prompt the user to provide a complexity level corresponding to a user characteristic, such as level of memory impairment. In some aspects, the platform may provide the user a number of attribute elements or steps corresponding to the complexity level. In other aspects, the platform may prompt the user to provide a number of attribute elements or steps. In further aspects, each of the attribute elements 202 may be assigned a default prominence or relevancy level. In the present example, attribute elements shown as L, or low impairment, may be assigned a prominence or relevancy level of 3, corresponding to attribute elements that have higher prominence or relevance to the theme of the visual presentation; attribute elements shown as M, or medium impairment, may be assigned a prominence or relevancy level of 2, corresponding to attribute elements that have medium prominence or relevance to the theme of the visual presentation; and attribute elements shown as H, or high impairment, may be assigned a prominence or relevancy level of 1, corresponding to attribute elements that have lower prominence or relevance to the theme of the visual presentation. To this end, a patient with low memory impairment may only need the two L attribute elements, which contain highly prominent and/or relevant content, to complete the visual presentation and corresponding activity or task; a patient with medium memory impairment may need the two L and three M attribute elements, which contain highly and medium prominent and/or relevant content respectively, to complete the visual presentation and corresponding activity or task; and a patient with high memory impairment may need the two L, three M, and three H attribute elements, which contain highly, medium, and lower prominent and/or relevant content respectively, to complete the visual presentation and corresponding activity or task. In some aspects, the platform may assign an adjusted or aggregate prominence and/or relevance value to each attribute element based at least on user behavior data and/or biometric data from the patient's interaction with the platform and visual presentation. In other aspects, the platform and/or a platform user may adjust or change the customized visual presentation between levels L (2 steps), M (5 steps), and H (8 steps) based at least on user behavior data and/or biometric data from the patient's interaction with the platform and visual presentation.

In another exemplary embodiment, FIGS. 3A-3B shows a customized visual presentation 300 with attribute elements 302 in an arrangement with each attribute element modified to contain content to reflect personalized information and details related to the theme, medication management in this example. Table in FIG. 3B provides additional detail related to the content contained within each attribute element for instructions for taking medication. In further aspects, the platform may receive selection criteria that may include "instructions" or "activity" for theme and "medication" as type, and a visual presentation template, matching the selection criteria may be provided to the user. The platform may then prompt the user to provide a low, medium, or high complexity level corresponding to a level of memory impairment. The platform may then provide the 2, 6, or 8 steps corresponding to the complexity level. In some aspects, the platform may prompt the user to provide a medication name or number of medications. In some aspects, the platform may assign an adjusted or aggregate prominence and/or relevance value to each attribute element based at least on user behavior data and/or biometric data from the patient's interaction with the platform and visual presentation. In other aspects, the platform and/or a platform user may adjust or change the customized visual presentation between levels L (2 steps), M (6 steps), and H (8 steps) based at least on user behavior data and/or biometric data from the patient's interaction with the platform and visual presentation. For example, all 3 levels may be completed and/utilized by a user to allow toggling between levels based on user clinical status and/or level of memory impairment.

By way of another non-limiting example, a customized visual presentation related to instructions for preparing oatmeal may comprise selection criteria "instructions" for theme and "Oatmeal" as instructions type, and thus, a visual presentation template matching the selection criteria may be provided to the user. The visual presentation may comprise a parent element represented by a shape and "Oatmeal" text, and a plurality of attribute visual elements linked to the parent element. Primary attribute elements may be linked to the parent element in a linked arrangement or layout. The attribute elements may be associates with steps of the instructions, including, "Kitchen", "Measure", "Pour and Stir", "Microwave", and "Enjoy!". In some aspects, an attribute element may comprise at least one of: a primary attribute element, a secondary attribute element, a tertiary attribute element, and so forth, which may correspond to complexity level. A first attribute element may comprise "Kitchen" as a primary attribute element, "Pantry" as a secondary attribute element with an image of the pantry, and tertiary attribute elements that include "middle shelf" with an image of oatmeal and "lower shelf" with an image of a measuring cup. Similarly, all of the plurality of attribute elements may be present at once in the linked arrangement for the user to modify content in each attribute visual element to reflect personalized information and details and/or add additional secondary and tertiary attribute elements. Alternatively, each attribute element may be individually presented to the user to modify or provide the relevant information or details and/or add secondary and tertiary attribute elements, and a personalized visual presentation is generated or composed upon providing all the necessary information for each attribute visual element. In further aspects, the customized visual presentation may further comprise an anchor point. The anchor point may comprise or be embodied in the form of an attribute visual element, and is configured to creates a sense of security, decrease stress and enhancing mood; or a sense of autonomy at having successfully completed a task independently. In further aspects, the anchor point can also serve as a reward to the user, for example, the reward of eating the oatmeal.

In further aspects, the platform can analyze or otherwise process the content and information contained in the visual presentation or template and, in response, it can determine a relevancy weight for each attribute visual element associated with a theme or template. In one aspect, the relevancy weight of an attribute element can be a numeric value representative of an importance or significance level (e.g., effect on behavior, stress, etc.) associated with an attribute or trait specific to a theme or template. In another aspect, the relevancy weight of an attribute element can be a visual representative (such as thickness of linking branch, sequence, or designated color) of an importance or significance level (e.g., effect on behavior, stress, etc.) associated with an attribute or trait specific to a theme or template. In yet another aspect, the relevancy weight of an attribute element can be a numeric value representative of a viewing time for the attribute visual element or element type. In some aspects, such value can be greater than or equal to zero and less or equal than the unity. In other aspects, to determine the relevancy weight of an attribute element, an analysis component can assign a value (e.g., a real number) of a predetermined function of the importance level for the attribute element to be indicative or prominent of the theme or template associated with the attribute element. In one embodiment, an interaction or viewing of a given attribute element may be extended, having a long viewing time, thus such view can be assigned a high relevancy weight in order to represent a low level of user recognition or preference with the given attribute element. The analysis component can retain information (e.g., data and/or metadata) indicative of one or more relevancy weights respectively associated with one or more attribute elements of a template or theme. The relevancy weight of various attribute elements can permit adjusting the number of attribute elements in order to establish a preference weight for a template or theme. In further aspects, the relevancy or significance of an attribute (or branch or steps) can be visually represented on the visual presentation. For example, the thickness of a linking branch can represent the relevant significance of that attribute to the central theme. Furthermore, designated colors and/or sequence ordering can be utilized to provide information related to theme, attributes, relevance and/or significance. In still further aspects, one or more of the default attribute elements in a visual presentation template may be deleted or adjusted by the user or the platform. For example, a selection criterion may be "level of cognitive impairment", the platform may remove or eliminate a given attribute element based on a cognition relevancy weight assigned to each attribute element, wherein the attribute element fails to meet a threshold relevancy to cognition level. To this end, a user that has been designated as having a high level of cognitive impairment may tolerate a limited number of attribute visual elements. Alternatively, a user may select to remove or add an attribute element based on observed historical behavior or other factor related to the end-user clinical condition.

Figure 4:
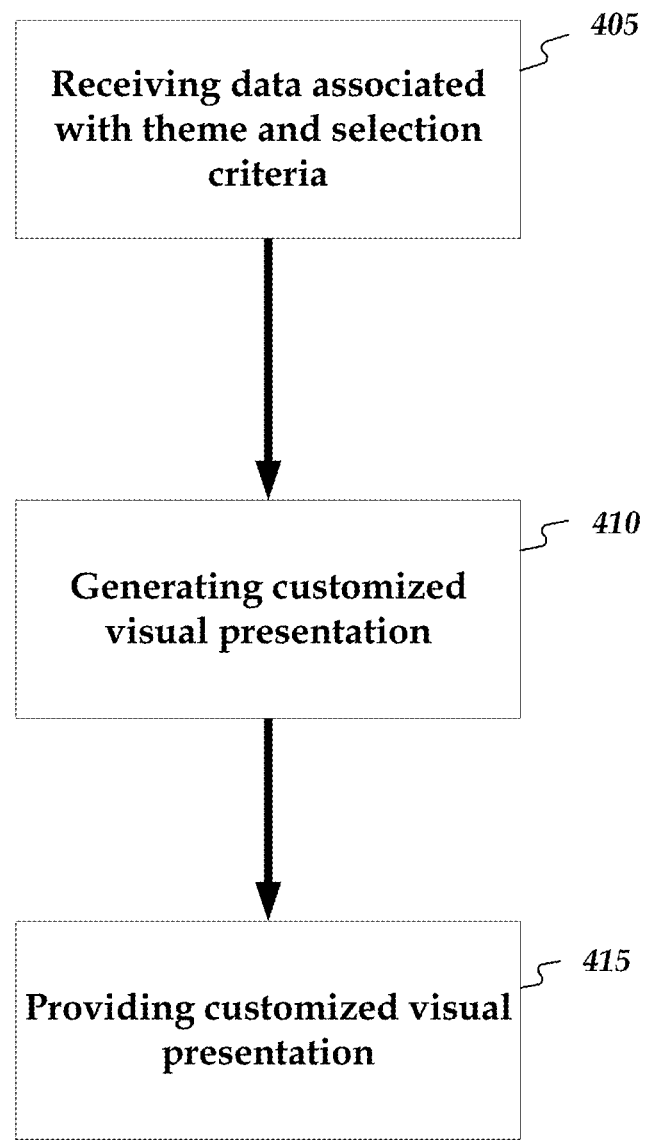
FIG. 4 illustrates a flow chart of a method for generating a customized visual presentation of the platform in accordance with an exemplary embodiment the present disclosure.
Figure 11A:
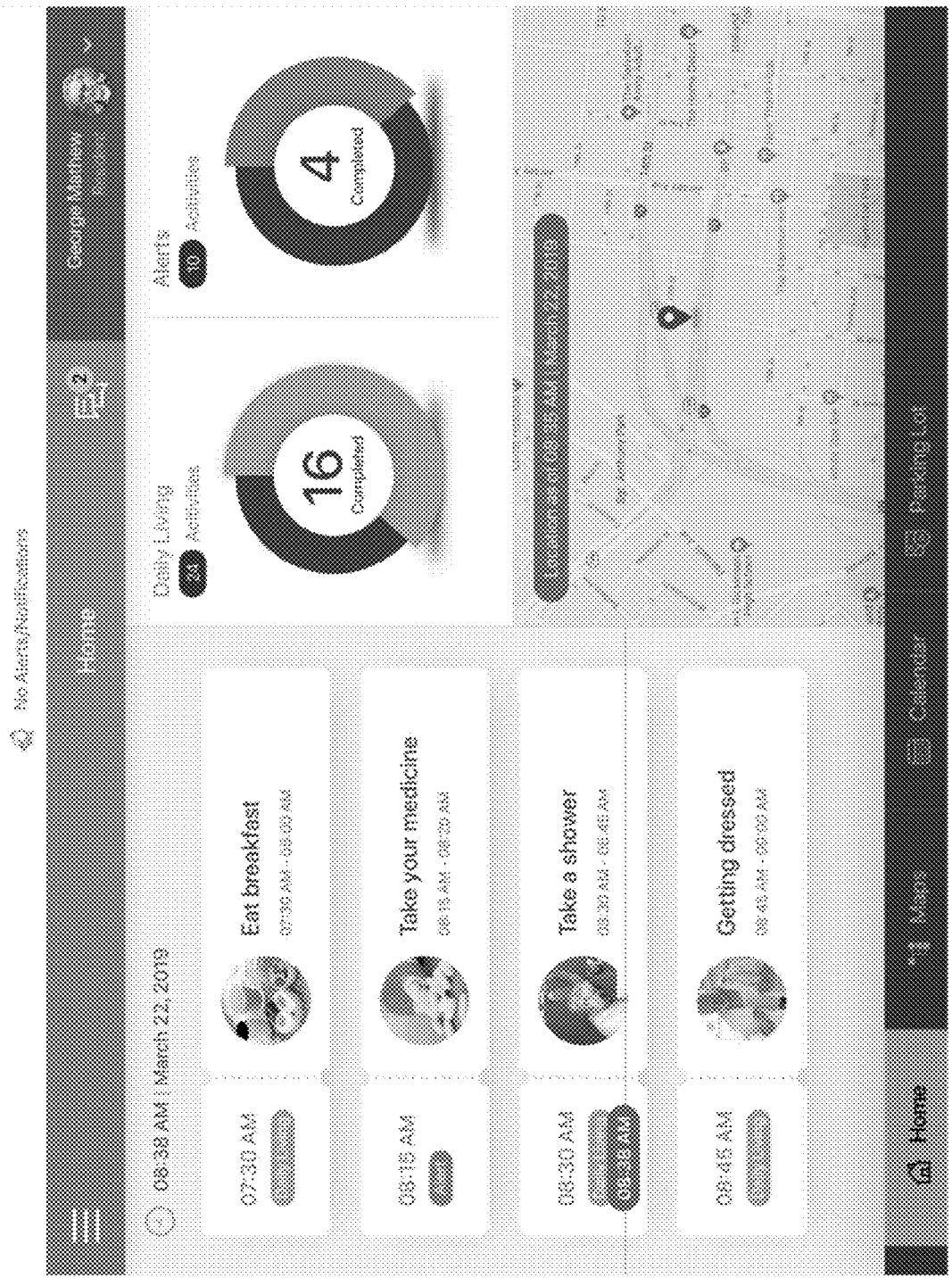
FIGS. 11A-11C illustrates dashboards for displaying various visual representations of the platform, customized visual presentation, user data, and/or analytical data in accordance with an exemplary embodiment the present disclosure.
Figure 11B:
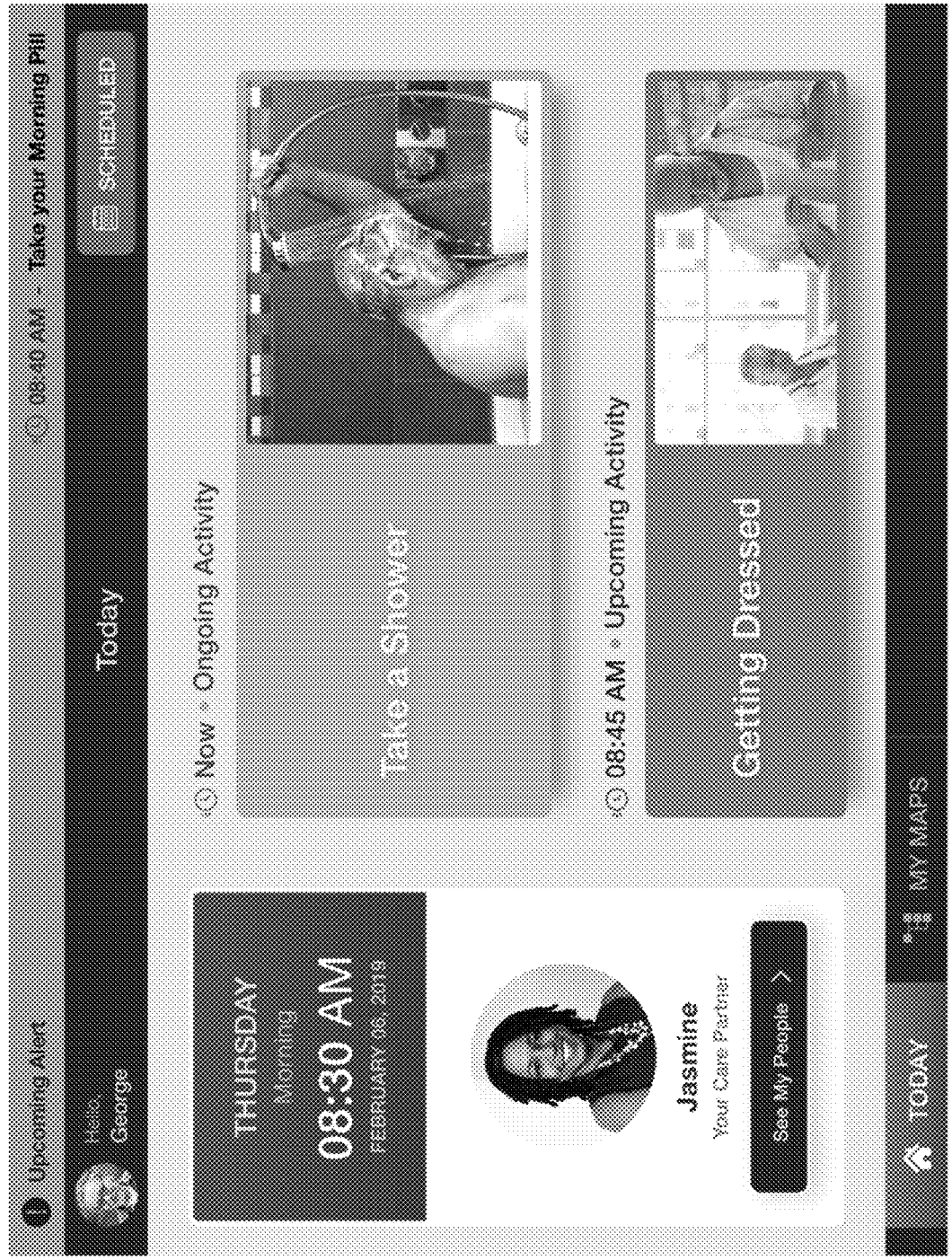
Figure 11C:
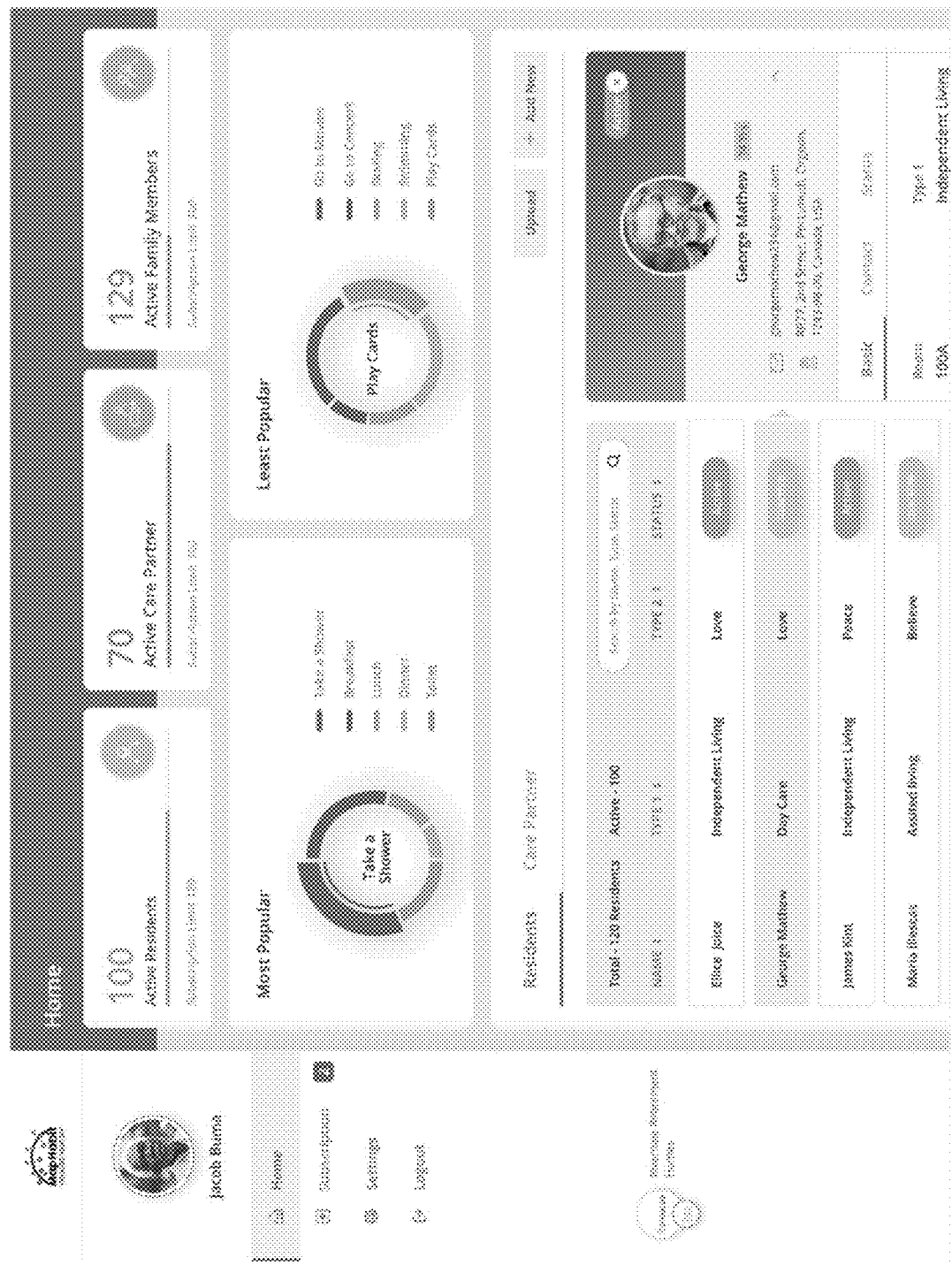

FIG. 4 is a flow chart setting forth the general stages involved in a method 400 for generating a customized visual presentation. Method 400 can be performed by visual presentation generation module 1622. Method 400 can also be implemented using a computing device 1600 as described in more detail below with respect to FIG. 13. Although method 400 has been described to be performed by computing device 1600, it should be understood that, in some embodiments, different operations can be performed by different networked elements in operative communication with computing device 1600. For example, server 110 and/or computing device 1600 can be employed in the performance of some or all of the stages in the disclosed methods. Moreover, server 110 can be configured much like computing device 1600 and, in some instances, be one in the same embodiment. Method 400 can begin at stage 405, wherein data comprising a theme and/or selection criterion can be received. The data can be received as, for example, a file accessible by computing device 1600. As described above, the data can be received or accessed from a database or repository. The data can be provided through a user interface, such as the user interface described herein. Alternatively, the user interface can have a section through which a file can be uploaded. Once computing device 1600 receives the data input in stage 405, method 400 can continue to stage 410 where computing device 1600 can generate a customized visual presentation using the input data. The customized visual presentation can be based on various visual presentation templates and keywords associated with attributes of the theme. Once computing device 1600 has generated a customized visual presentation at stage 410, method 400 can continue to stage 415 where computing device 1600 can provide or display the customized visual presentation. In some aspects, dashboards, such as dashboards shown in FIGS. 11A-C, may be provided to display various visual representations of the platform, customized visual presentation, user data, and/or analytical data described herein. In further aspects, a standard set of views and templates may be used to display the customized visual presentations and/or the associated data. In still further aspects, the dashboard may comprise a plurality of dashboard views for each user type (patients, family members, caretakers, clinicians, and/or facilities) that allows platform users to set configuration properties to customize the customized visual presentations, views, graphs, and/or charts. In yet further aspects, these configurations may include, for example, an attribute identifier, a feature identifier, branch grouping, single or multiple, aggregate function, default and customizable labels. The dashboard may also include the ability to define baselines, which may be used to provide visual cues on the presentations and for alarms or notifications relating to a patient or user interaction with the customized visual presentations. In further aspects, platform can provide the customized visual presentations to the user, a caregiver or physician office. For example, the platform may facilitate delivery of customized visual presentations to caregiver or physician office, for example, the day before a scheduled visit.

In still further aspects, a number of standardized neuropsychological assessment tools may be used to measure the initial and subsequent clinical status of the user, for example, a severity of memory impairment may be determined by assessment (Wechsler Memory Scale—Revised [WMS-R], Warrington Recognition Memory Test [WRMT], and the Doors and People Test [D&P]). The clinical status can be used to provide the patient and the non-patient platform user with an initial and subsequent burden level they face with respect to the challenge of impaired memory. Memory impairment may be associated with the development of negative emotional states that grow concurrently with impaired memory. In particular, patients with Alzheimer's disease and other conditions that impair memory commonly report feeling frustrated, stressed, angry, anxious and confused. Moreover, they experience poorer quality of sleep, engage in less physical activity, and frequently are diagnosed with comorbid chronic depression. It is important to note that a diagnosis of chronic emotional stress and impaired emotional states are commonly seen in caregivers as well. Accordingly, discussion of the burden of emotional dysfunction applies to both patients and caregivers. Further, as is the case for memory impairment, the burden of impaired emotional states, can be readily and systematically assessed using standardized neuropsychological measurement tests. For example, additional standardized neuropsychological measurement tests that may be used in the platform may include the Patient Health Questionnaire (PHQ-9), which assesses a wide range of symptoms associated with depression (9 questions: Little interest in doing things? Feeling bad about yourself?; Feeling tired or having little energy?); the Generalized Anxiety Disorder (GAD-7), which assesses generalized anxiety (7 questions: Feeling nervous, anxious, or on edge? Becoming easily annoyed or irritable?); and the Repeatable Battery for the Assessment of Neuropsychological Status (RBANS), a brief test to detect cognitive decline.

In yet further aspects, the platform may utilize a number of objective and systematic tools to diagnose and assess the patient, such as, patient's memory impairment as well as the emotional dysfunction that accompanies impaired memory. Moreover, emotional dysfunction is one that applies to caregivers as well. In this sense, by reducing the emotional burden of the caregiver as well as the patient, the methods and systems of the present invention can have a measurable and significant positive impact on quality of life measures for both patients and caregivers. Additional problems and challenges are the cost of health care for hospitals and physician offices. Part of this cost comes from a failure of compliance both in terms of appointments as well as in terms of compliance with medications and instructions. In further aspects, use of customized visual presentation, and specialized templates of the present platform can reduce such costs, for example, the cost of care and the cost of administering personalize care to individualized patients. In yet further aspects, use of the disclosed customized visual presentation of the present platform can allow for a higher patient visit throughput with better communication so that patients will be more compliant.

Figure 5:
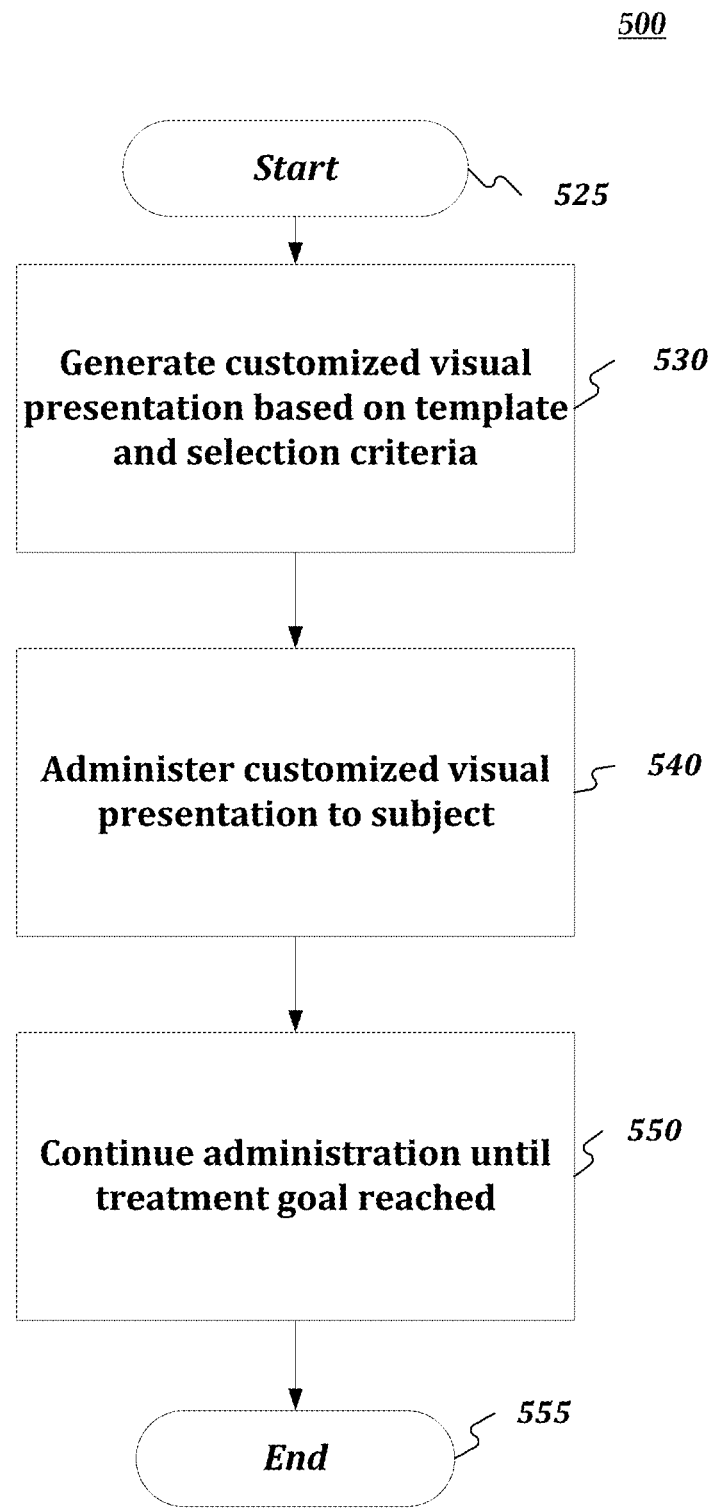
FIG. 5 illustrate a flow chart of a method for treating memory impairment using a customized visual presentation of the platform in accordance with an exemplary embodiment the present disclosure.

As described herein, the inventive devices, systems, techniques and methods of the present platform can draw upon customized visual presentation and can be used to improve memory and/or treat memory impairment, such as in dementia and/or Alzheimer's disease. FIG. 5 show flow charts setting forth the general stages involved in a method 500 for treating memory impairment consistent with an embodiment of the disclosure for providing the platform 100. Various stages of method 500 can be implemented using a computing device 1600 as described in more detail below with respect to FIG. 13.

Although method 500 has been described to be performed by platform 100, it should be understood that computing device 1600 can be used to perform the various stages of method 500. Furthermore, in some embodiments, different operations can be performed by a user or different networked elements in operative communication with computing device 1600. For example, server 110 can be employed in the performance of some or all of the stages in method 500. Moreover, server 110 can be configured much like computing device 1600. Although the stages illustrated by the flow charts are disclosed in a particular order, it should be understood that the order is disclosed for illustrative purposes only. Stages can be combined, separated, reordered, and various intermediary stages can exist. Accordingly, it should be understood that the various stages illustrated within the flow chart can be, in various embodiments, performed in arrangements that differ from the ones illustrated. Moreover, various stages can be added or removed from the flow charts without altering or deterring from the fundamental scope of the depicted methods and systems disclosed herein.

Method 500 can begin at starting block 525 and proceed to stage 530 where platform 100 can generate customized visual presentation based on inputted data, template and selection criteria associated with platform 100. Inputting can comprise the stages of importing and mapping the data by accessing various sources, for example, user profile, electronic medical record, template and/or image repository or database. Consistent with the embodiments of the present disclosure, platform can be configured to consolidate data from multiple sources and disparate formats. Platform can be configured to communicate with the various data sources via, for example, an application programming interface integration between platform 100 and the data source. In this way, data integration can be at least in part computer-implemented. From stage 530, platform can advance to stage 540 where the customized visual presentation is administered to a subject, such as a patient. Various views and or formats can be provided through a user interface of platform, such as those shown in FIG. 11A-11C. Method 520 can continue to stage 550 where platform can enter into an administration or implementation mode, wherein the customized visual presentation can be continued to be provided or administered to the subject or patient until a treatment goal or outcome is achieved. For example, platform can provide or display the customized visual presentations to the user as part of a program, such as memory training program. For example, the platform may facilitate administration of a program or treatment regimen and monitor use and track progress of the user or subject.

In various further aspects, the present invention also provides methods for preventing memory impairment in a subject. To treat or control the memory-related disease or disorder, the treatments are administered to a subject in need thereof, such as a human. In a further aspect, the subject has been diagnosed with a need for memory impairment treatment prior to the administering step. In a still further aspect, the subject has been diagnosed with a memory-related disease or disorder associated with age-related memory loss. Prior to administering the treatment, the subject can be diagnosed with a need for treatment of memory-related disorder or disease, such as dementia. In a still further aspect, the subject can be identified with a need for treatment of memory impairment treatment, as described herein. The treatment can be administered to the subject according to any method, such as a computer implemented or the like. In determining the effective amount of use of the invention, a response to a prophylactic and/or treatment method of the invention can, for example, also be measured by determining the behavioral and/or physiological effects of the treatment, such as the decrease or lack of disease symptoms following administration of the treatment. Other assays will be known to one of ordinary skill in the art and can be employed for measuring the level of the response. For example, the diagnostic methods that are used to ascertain the likelihood that a subject has a memory-related disorder or disease can be used to ascertain the level of response to a prophylactic and/or treatment method of the invention. The amount of a treatment may be varied for example by increasing or decreasing the amount of treatment. The effective amount will vary with the particular condition being treated, the age and physical condition of the subject being treated, the severity of the condition, the duration of the treatment, the nature of the concurrent therapy (if any), and the like factors within the knowledge and expertise of the clinician or health practitioner. For example, an effective amount can depend upon the degree to which an individual has abnormal impairment levels and/or activity. In some aspects, the effective amount is a therapeutically effective amount. In other aspects, the effective amount is a prophylactically effective amount. In further aspects, the subject is a mammal, preferably a human.

In further aspects, the method further comprises the step of identifying a subject in need of memory impairment treatment. In a still further aspect, the subject in need of memory impairment treatment comprises having at least one risk factor for developing a memory-related disease or disorder. In another aspect, a method of diagnosis comprises performing an experiment upon the subject and/or identifying a level of a biological marker. In another aspect, a method of diagnosis comprises performing an assessment upon the subject. In various aspects, a method of the platform may include performing an assessment on the platform user, and may comprise gathering biometric data from the patient. In still further aspects, an assessment may comprise multidimensional set of measures which provides assessments in cognition, emotion, motor, and sensation.

As described herein, the present platform and methods can be effective to create habit memory formation and support habit regions of the brain. Everyday conscious memory, often called declarative memory, is based on active learning and conscious memorization, and is dependent on a region of the brain in the temporal lobe that includes the hippocampus. When the hippocampus and related brain structures are damaged or destroyed, as in the case of Alzheimer's disease, the individual loses the ability to learn new memories and to consciously access recent memories (declarative memory). By contrast, habit learning occurs when information is stored unconsciously, through repetition and trial-and-error learning. These memories are believed to be managed in a different region of the brain called the neostriatum. In further aspects, the habit regions of the brain can support the capacity to learn and retain new information unconsciously, retaining habit memory even when conscious or declarative learning is absent, as in the case of amnesia from Alzheimer's disease.

Figure 12:
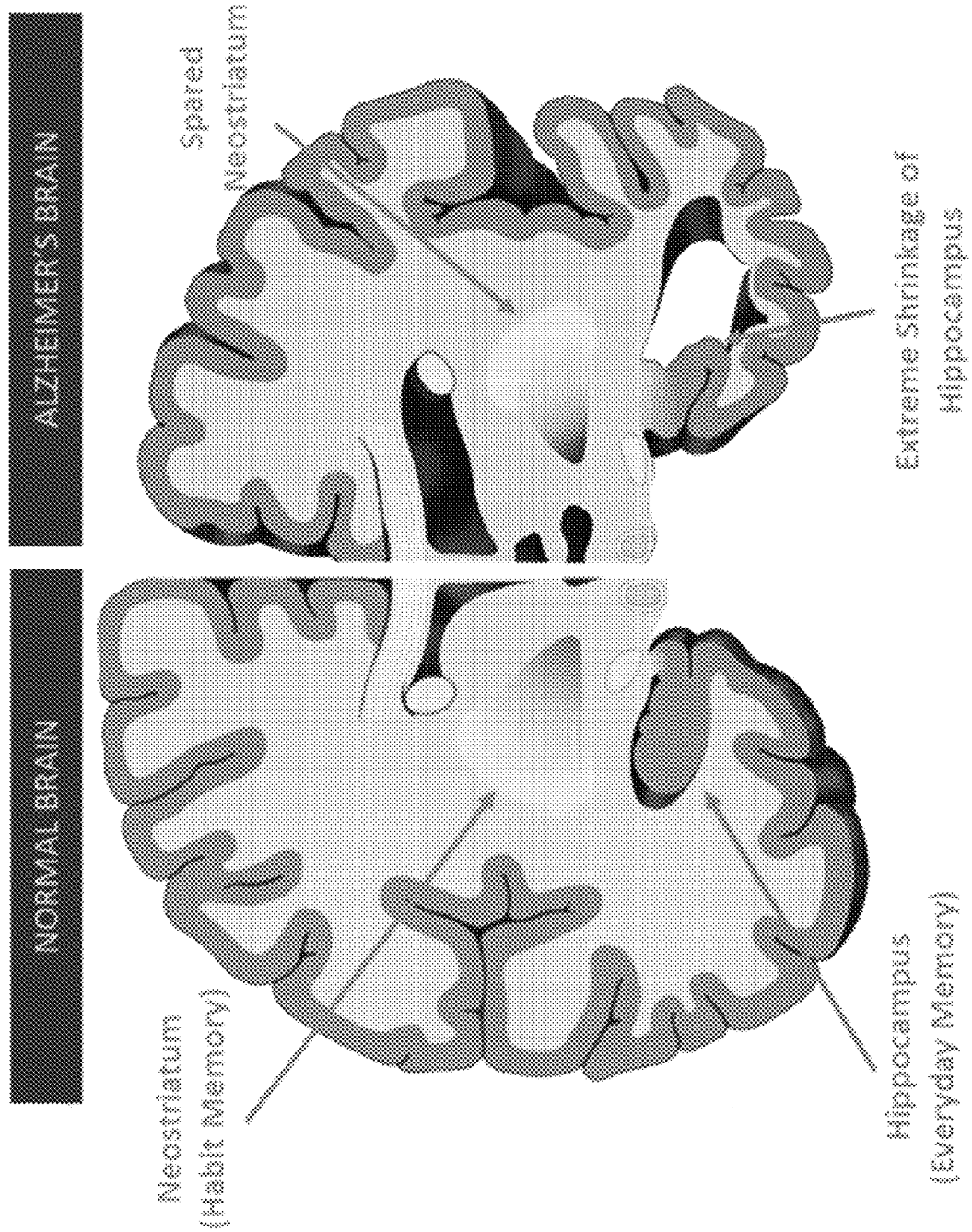
FIG. 12 illustrates brain structure of normal brain and Alzheimer's brain.

In various aspects, methods and techniques of the present platform can utilize the intact neostriatal system to bypass the impaired hippocampal declarative memory system. With repeated experience, memory-impaired individuals can learn to routinely utilize visual presentations of the platform, even though they might have no conscious recollection (declarative memory) of having learned to use the visual presentations. In further aspects, the platform focused treatment on the neostriatum and habit memory has several advantages over more typical approaches that attempt to instead bolster the everyday memory (hippocampal) system for memory-impaired individuals. As shown in FIG. 12, the hippocampus shows evidence of pathology in the form of plaques and tangles early in the diagnosis of Alzheimer's disease (AD), corresponding to the behavioral symptom of impaired memory as the most common early defining marker of AD. By contrast, the neostriatum does not show these pathological markers for a much longer time (often years) from diagnosis. The present platform is effective in utilizing spared regions of the brain to develop habits related to various ADLs encompassed in the visual presentations, and in this way, can lessen the impact on memory of the damaged hippocampal system. Further, the hippocampal system is an initial and primary target of the pathology of AD, and it becomes progressively more deteriorated as the disease advances. Accordingly, the hippocampus is progressively less useful as a target for behavioral intervention, while the neostriatum remains spared for a longer time into the disease and is a more appropriate target for behavioral intervention. To this end, the neostriatum can convert a sequence of actions, such as those described in connection with the disclosed methods and system herein, into an automatic routine, a habit. The process within the brain comprise a three-step loop, and can be used in conjunction with the platform to target these habit brain regions. In further aspects, the disclosed methods may first provide a cue, a trigger, or stimulus configured to cause the brain to go into automatic mode and use a habit. Next, a routine habit may be provided, such as in a visual presentation, or which can include physical, mental or emotional activity. For example, a disclosed routine of the present platform can comprise a patient utilizing the visual presentation or map. Finally, the platform may then provide a reward to the patient, which can help the brain figure out that a particular loop is worth remembering. In further aspects, this loop method—cue, routine, reward can become more and more automatic, and can become a habit. In yet further aspects, cues can comprise a tone or flashing light stimulus, or a vibration from a wrist device or band. In still further aspects, routines can include individual looking at the visual map, and being guided by the information contained therein. In even further aspects, a reward may include a reduction in stress, a sense of autonomy, or a clearer understanding.

According to various further aspects, methods of the platform may include a setup or 'on-boarding' phase, in which targeted user behavior data and themes for a patient may be determined. In some embodiments, determining targeted user behavior data and themes may be performed automatically by scraping/parsing a patient's user activity history within the platform for key elements. In further aspects, the platform user may provide inputs indicating the target user behavior data, biometric data, and/or patient information.

In various aspects, key elements associated with one or more attribute element pages and/or visual presentations may be determined. These key elements may then serve as a base reference point when analyzing future interactions and/or other pages to track an individual patient's progress, develop models of trajectories through illness, make predictions about clinical status, and/or determine in-need status for a patient. In further aspects, the platform may use a base reference point to perform one or more stages in the disclosed methods. In various embodiments, the platform ability to track individual user behavior and transmit to servers may be built directly into a software application installed on the user device. When a potential in-need user of the platform (hereinafter referred to as a "in-need patient") visits a page, computer code on the user device may execute one or more stages of a disclosed method, for example, the code may search for a monitor or tracker on the user device associated with the patient. The code may assign a unique identifier (ID) to the patient if no unique ID has been previously assigned. Subsequently, the code may store a tracker on the patient device with the ID, among other information. On the other hand, if a tracker is found on the patient device, the unique ID stored on the device is retrieved. In this case, this information may have been previously stored when the patient device accessed a page and/or any other visual presentation on the device in the past.

During an on-boarding or setup phase for clinician platform use, a platform user may provide at least one of the following: 1) a list of targeted input user data (which may include, but not be limited to, at least one non-personally indefinable data point for the patient); and 2) areas of targeted clinical interest (which may include, but not be limited to, for example user behavioral variables, neurobehavioral measures, and/or keywords associated with the area of clinical interest). In other embodiments, a platform user may provide a desired threshold 'confidence level' associated with the areas of targeted clinical interest. To this end, the platform may be enabled to assess the universe of unique IDs to determine which of those unique IDs may be associated with a threshold confidence level for key elements corresponding to the area of targeted clinical interest.

Consistent with various embodiments, a method of the present platform may begin at a stage which may include identifying and/or logging a list of pages which were previously visited by the patient represented by a unique ID of interest. Moreover, the platform may be enabled to maintain or access an up-to-date list all pages visit by the identified patient after a triggering event. The method may include a stage of automatically accessing each page from a list of visual presentations and parse the content on each page for key elements. Key elements, as used herein, may include, but not be limited to, text, images, video, audio, and combinations thereof. In some embodiments, the page may have been previously processed in accordance to this stage. Additionally, the method may include a stage of aggregating the key elements from the list of pages. In some embodiments, the page may have been previously processed in accordance to this stage. Further, the method may include a stage of analyzing the key elements. As one example of an analysis stage, the platform may be configured to assign scores to key elements in order to determine if there are any key elements that are associated with a set of reference key elements (e.g., established during a setup or onboarding phase). As such, the scores may be assigned based on a comparison between the key elements and the reference key elements obtained during a setup phase. Furthermore, the method may include identifying one or more patterns in the key elements. The one or more patterns may be identified based on the raw data comprising the key elements, machine learning, AI processing of the key elements and so on. It should be understood that the method of 'scoring' is only one of many possible techniques to perform an analysis consistent with the present disclosure.

Additionally, in some instances, the method may further include a stage of adding a weight to more recent key elements. In other words, the method may incorporate a time factor. Accordingly, for instance, if more than two attribute element pages with recent key elements are identified, such key elements are identified as 'younger key elements' and accordingly given a higher weight in determining whether the patient is clinically in-need. It should be understood that the method of 'weighting' is only one of many possible techniques to perform an analysis consistent with the present disclosure. For example, if the patient visited two attribute element pages containing content on medication within a predetermined period of time (e.g., may be established during creation of the customized visual presentation, such as during a setup or onboarding phase), then they may be determined to be in-need for clinical intervention related to managing their medication. Upon analysis, the method may further include a stage for determining the in-need (e.g., propensity) status of the patient. To this end, a corresponding data field associated with the unique ID may be set to 'true,' or 'in-need,' or 'needs evaluation'. Further, according to various embodiments, the method may include cross referencing the patient with an Electronic Medical Record (EMR) database associated with a platform user, such as the patient and/or heath care organization. For example, data associated with the patient may be stored in a record associated with the patient in the EMR database. Data associated with the patient may include, but not limited to, data related to the medical history, clinical data, biometric data, historical platform data of the patient along with respective confidence values, key elements, the list of visual presentations visited etc. The data may further include user behavior data and neuro-behavioral assessments for each cross-referenced patient in the EMR database. This may be done based on, for example, a common reference point. For example, the login provided by the patient may be associated with a medical record number of the patient as stored in the EMR database. Other common reference points may be used, such as, for example, but not limited to address, phone number, and other non-PHI (Protected Health Information) and/or PHI cross-reference elements.

In some embodiments, the method may include triggering a clinical assessment based on the in-need status of the patient. For example, the clinical assessment may include be carried out on one or more channels such as, through the platform, SMS, messaging within a software application, telephonic calls, video calls, in-person evaluation, etc. In various embodiments, the method stages may be repeated for dynamically updated lists of pages the patient has been determined to have visited. In such update, the data fields and associated user data may be modified based on the new data.

Figure 7A:
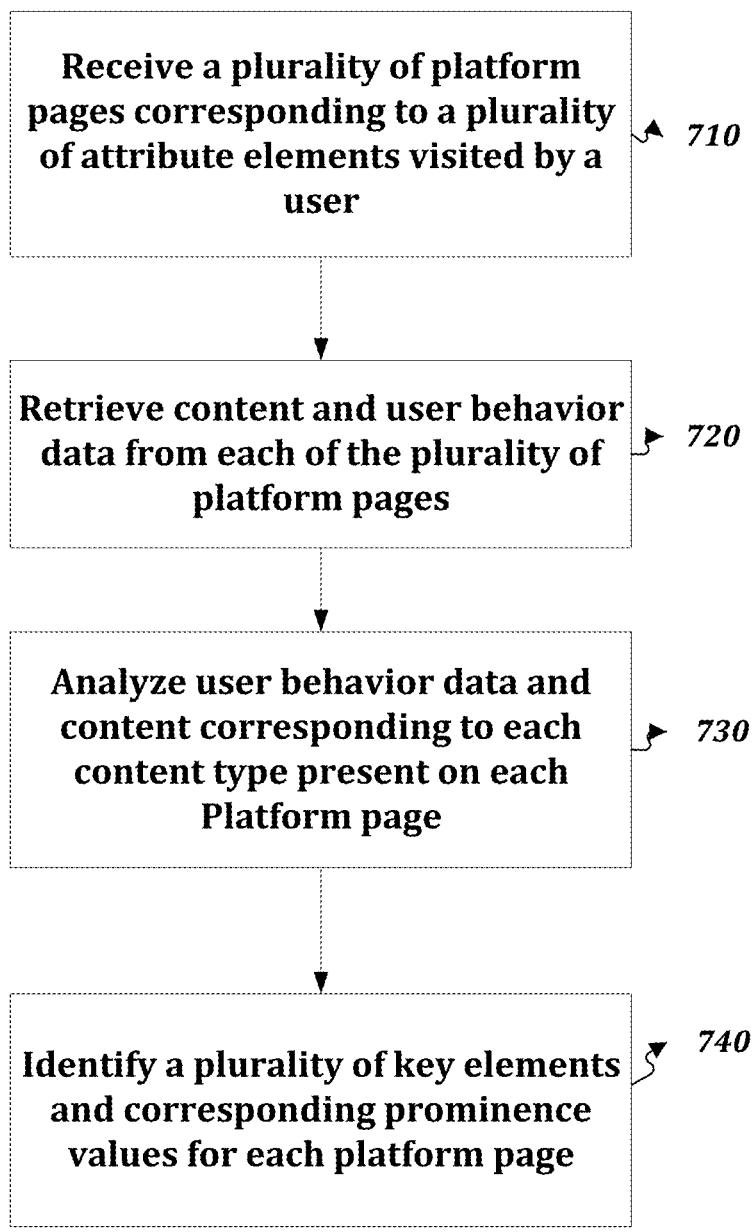
FIGS. 7A-7C illustrates method for creating a user profile based on user behavior in accordance with an exemplary embodiment the present disclosure.
Figure 8:
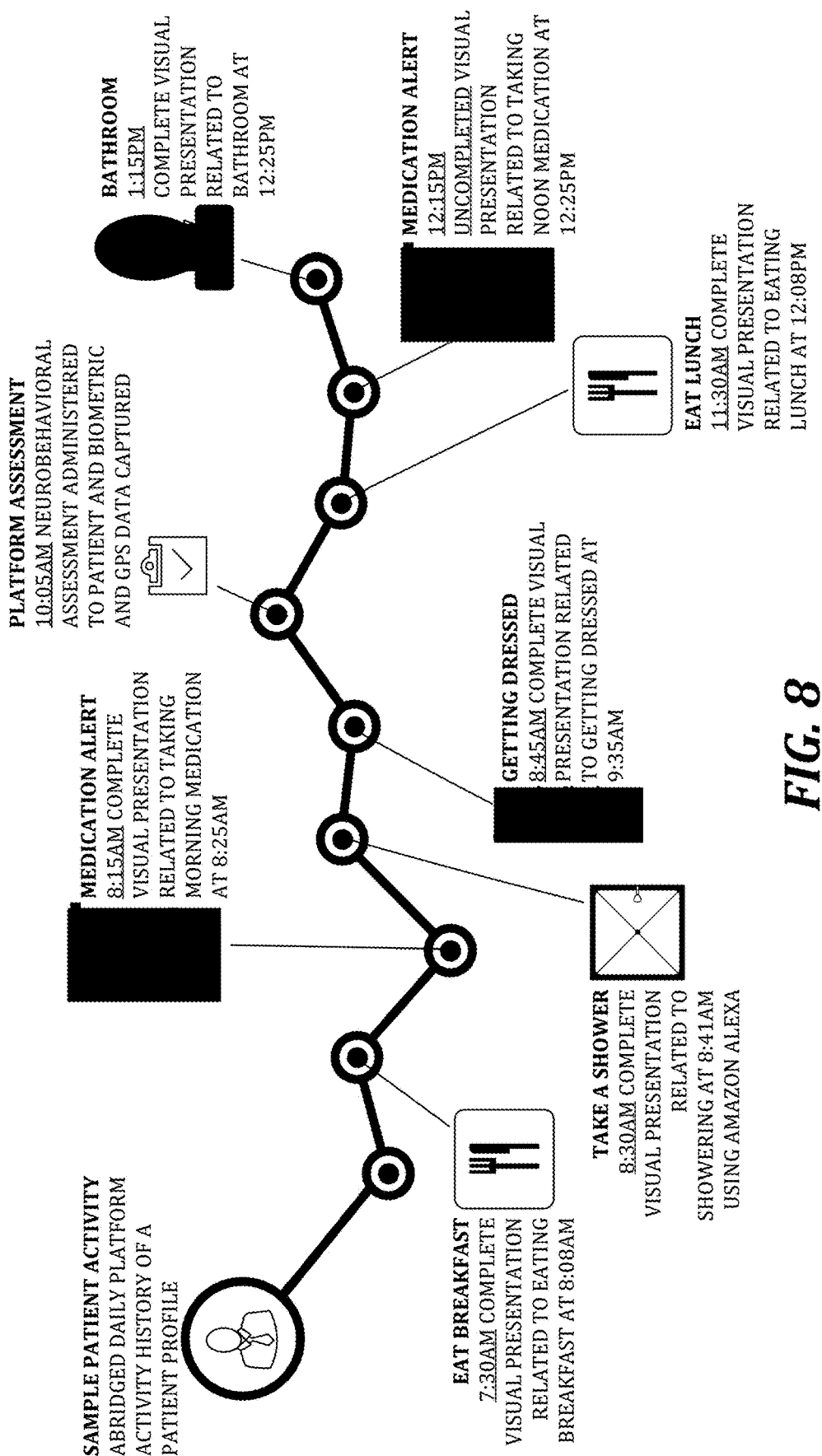
FIG. 8 illustrates a platform user behavior of a user based on which a user profile may be created in accordance with an exemplary embodiment the present disclosure.

According to further embodiments, the platform may employ a computer implemented method, such as method 700A, of creating a profile of a user based on user behavior may be provided as illustrated in FIG. 7A. The user behavior may include for example, platform activity performed by the user such as interacting with visual presentations, biometric data associated with user, completing tasks, downloading content from the platform, uploading content to the platform and interacting with a desktop application and/or a mobile application. As an example, user behavior data and biometric data based on which the user profile may be created is illustrated in FIG. 8.

Further, in some embodiments, data representing the user behavior may be de-identified. In other words, data representing the user behavior may not include identifiable information such as name, and so on. Accordingly, privacy of users may be preserved. In order to create the user profile, the method may include a step 710 of receiving a plurality of platform pages (e.g., user interface screens) corresponding to a plurality of attribute elements from one or more visual presentations interacted with by the user. Further, the method may include a step 720 of retrieving user behavior data and content from each of the plurality of visual presentations based on the platform pages. For instance, a monitor program may be executed on a processor to automatically retrieve user behavior data and content from each of the plurality of visual presentations by monitoring the plurality of platform pages.

Subsequent to retrieving the content, the method may include a step 730 of analyzing the user behavior data and content from each of the plurality of visual presentations. In some embodiments, analyzing content from a visual presentation may include analyzing content corresponding to each content type present on the visual presentation. For example, both textual content and non-textual content such as audio, images, video and multimedia on the visual presentation may be analyzed.

Further, in some embodiments, the analyzing may include performing natural language processing (NLP) of a textual content in the visual presentation. Additionally, in some embodiments, in case the visual presentation consists of non-textual content, a step of converting the non-textual content into textual content may be performed. Subsequently, the NLP may be performed on the converted content. By way of non-limiting example, content of the visual presentation may be analyzed using, for example, NLP and may result in identification of a theme or category of content, such as "Medication". Further, NLP may also identify other characteristics of the visual presentation, such as for example, "Morning pill" that may provide a greater contextual relevance and awareness to users. Additionally, NLP may also include event detection involving identification of specific time-sensitive triggers or alerts, such as for example, an upcoming "Scheduled Medication". Further, NLP may also identify important topics addressed in the content of the visual presentation and associate those topics as concept tags with the visual presentation, such as for example, ADLs related to "Showering". Further, NLP may also include entity extraction involving identifying relevant proper nouns like people and/or places.

Additionally, the method may include a step 740 of identifying a plurality of key elements, such as for example keywords, corresponding to the visual presentation based on the analyzing. For instance, a user-specific set of keywords may be identified for a user based on the user's interaction with various customized visual presentations. For example, based on the user's viewing of a visual presentation related to medication management, the keywords "Pill" and "Swallow" may be identified and associated with the user.

Furthermore, the plurality of keywords may be associated with a plurality of prominence and/or relevancy values. The plurality of keywords and the plurality of prominence and/or relevancy values may constitute the profile of the user. For instance, a prominence and/or relevancy value of the keyword in a visual presentation may represent how strongly the content of the visual presentation relates to the keyword. In other words, the prominence and/or relevancy value may represent a relative importance of the keyword in the content. Accordingly, in some instances, keywords that appear in important attribute element pages of the visual presentation may be associated with a relative larger prominence and/or relevancy value as compared to those keywords that appear in less important attribute element pages in the visual presentation. Likewise, keywords that appear often within the content of the visual presentation may be associated with a relatively larger prominence and/or relevancy value as compared to those keywords that appear only once or a few times. Additionally, keywords that may appear in different media types present on the visual presentation, such as text, image and audio/video may be associated with an even higher prominence and/or relevancy value.

Figure 7B:
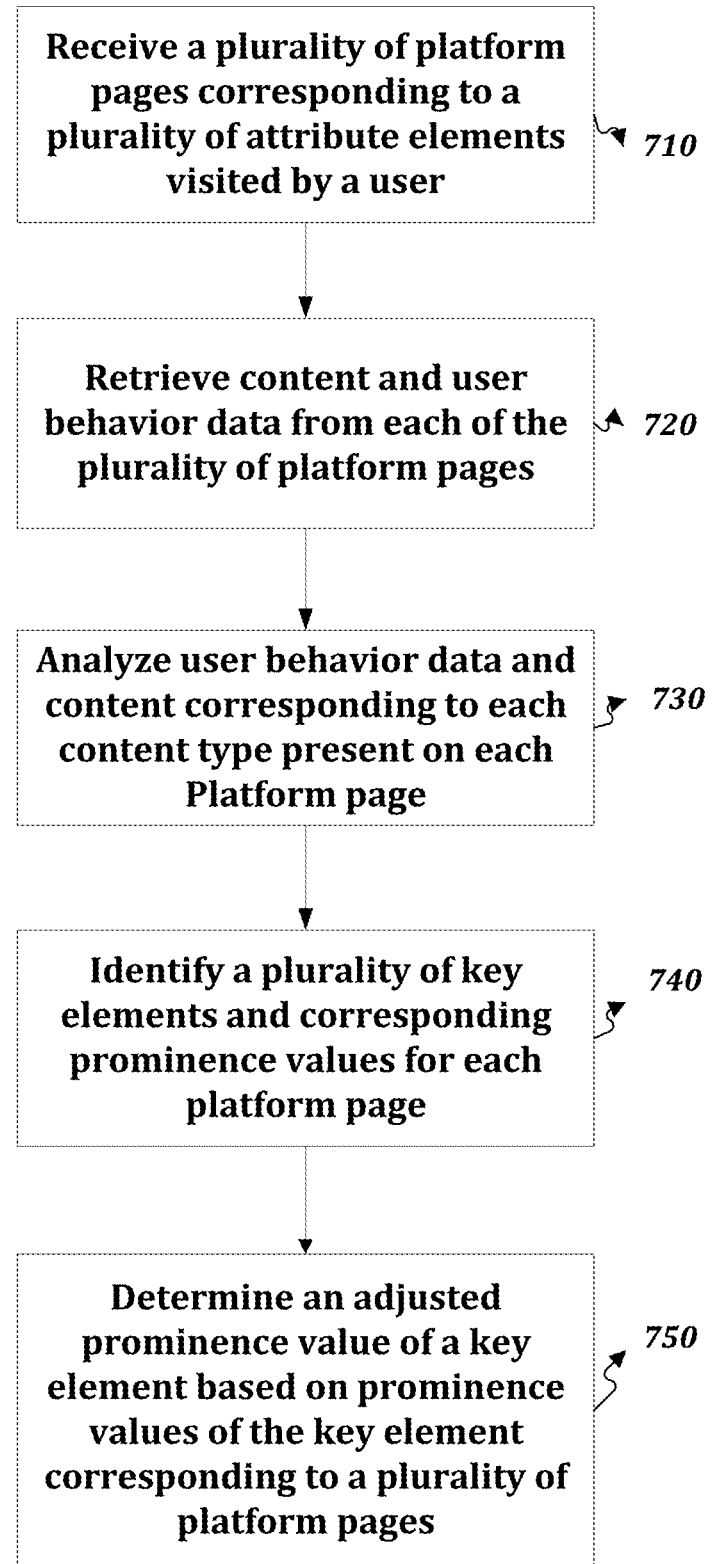

Further, in some embodiments, as illustrated in FIG. 7B, the method may further include a step 750 of determining an aggregated prominence and/or relevancy value corresponding to a keyword based on a first prominence and/or relevancy value of the keyword corresponding to a first attribute element page of a visual presentation and a second prominence and/or relevancy value of the keyword corresponding to a second attribute element page of a visual presentation. In other words, the aggregated prominence and/or relevancy value may represent an overall prominence and/or relevancy of the keyword to the user based on the user's interaction with a plurality of attribute element pages within a visual presentation containing the keyword.

Further, in some embodiments, the aggregated prominence and/or relevancy value may further be based on a time decay value associated with each of the first prominence and/or relevancy value and the second prominence and/or relevancy value. For instance, each of the first prominence and/or relevancy value and the second prominence and/or relevancy value may be weighted based on a time decay value. Accordingly, an impact of a prominence and/or relevancy value on the aggregated prominence and/or relevancy value may be controlled according to for example, a freshness associated with the prominence and/or relevancy value. For instance, a prominence and/or relevancy value of the keyword associated with a first visual presentation accessed a day ago may be weighted more than a prominence and/or relevancy value of the keyword associated with a second visual presentation visited a month ago.

Figure 7C:
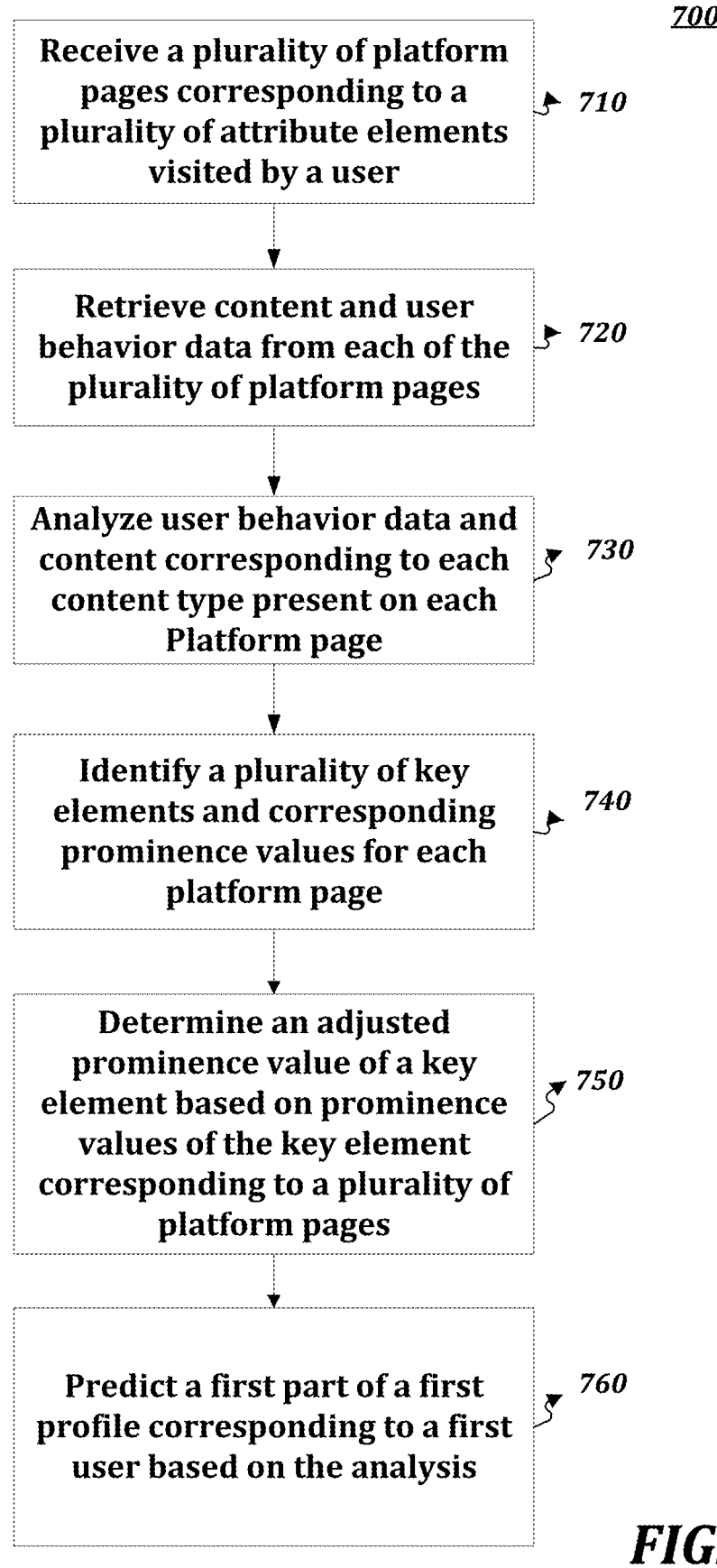

Accordingly, the time decay value, in some embodiments, may take into account the dynamic nature of user activities. In other words, keywords from visual presentations visited a day ago may represent a current need or changing clinical status of a user which may be stronger than a past interest represented by keywords from visual presentations visited a month ago. Consequently, prominence and/or relevancy values corresponding to these keywords may be weighted relatively higher in relation to those of keywords from visual presentations visited a month ago. Further, in some embodiments, as illustrated in FIG. 7C, the method 700C may further include a step 760 of predicting a first part of a first profile corresponding to a first user based at least on the prior analysis and/or on a first part of the second profile corresponding to a second user. Additionally, the predicting may be based on a result of a comparison between a second part of the first profile and a second part of the second profile.

Accordingly, a profile of a user may further include one or more characteristics of the user, such as age, disease, or gender. Accordingly, in some embodiments, the first part may include one or more characteristics of the first user. Further, the second part may include at least one keyword and one or more corresponding prominence and/or relevancy values. Accordingly, based on a match of keywords and prominence and/or relevancy values of the first user and that of the second user, one or more characteristics, such as demographic characteristics, of the second user may be predicted based on the one or more characteristics of the first second user. In other words, based on a match of keywords and/or prominence and/or relevancy values between two users, one or more characteristics of one user may be associated with the other user.

Additionally, in some embodiments, the first part may include one or more keywords and one or more corresponding prominence and/or relevancy values. Further, the second part may include one or more characteristics of the first user. Accordingly, based on a match of one or more characteristics of the first user and that of the second user, one more keywords and/or corresponding prominence and/or relevancy value of the second user may be predicted based on one or more keywords and/or corresponding prominence and/or relevancy values of first second user. In other words, based on a match of, for example, demographic characteristics between two users, keywords and/or corresponding prominence and/or relevancy values of one user may be associated with the other user.

Further, in some embodiments, a result of comparison of a keyword and a corresponding prominence and/or relevancy value corresponding to each of the first user and the second user may be associated with a confidence value. Additionally, the predicting may be associated with an aggregated confidence value computed based on aggregating confidence values corresponding to each keyword and corresponding prominence and/or relevancy value of a plurality of keywords and corresponding prominence and/or relevancy values.

According to various aspects, the benefits of the platform can provide many advantages for many different patients and applications. In further aspects, the platform can address many existing problems and challenges that commonly occur patients with impaired memory have, such as physician visits. In still further aspects, the users and patients of the platform can now have a greater ability to have meaningful discussions with others, such as physicians and caregivers, because at least patient concerns are developed ahead of time on the personalized visual presentation and can be readily accessed for the critical information related to the activity. Prior to the inventive platform, a medical provider would have to rely on the patient (or caregiver/family member) verbal recollection of the experience. Thus, in some aspects, the platform can facilitate interaction with physician and patient, and can provide communication means and tools that are clearer than traditional patient-clinician interaction.

Without wishing to be bound by a particular theory, evidence exists that suggests patients can be more compliant in terms of both appointments and their medication regimen as well as with other instructions from the physician through the use of visual maps such as those provide through the present platform. Further, additional evidence exists suggesting patient can exhibit and experience less stress, family members can be more engaged in the patient's course of treatment, and the burden on the primary caregiver can be decreased. In further aspects, the burden can comprise various kinds of challenges that must be managed by the caregiver. In one aspect, a first kind of burden can be the memory impairment of the individual for whom they are caring. For people with Alzheimer's disease, for example, simply remembering an appointment or taking their medication at a particular time or remembering a new person's face or following the course of a conversation become progressively more daunting as the disease continues to develop.

D. Platform Architecture

The platform 1620 and visual presentation generation module 1622 can be embodied as, for example, but not be limited to, a website, a web application, a desktop application, and a mobile application compatible with a computing device. The computing device can comprise, but not be limited to, a desktop computer, laptop, a tablet, or mobile telecommunications device. Moreover, the platform 1620 and visual presentation generation module 1622 can be hosted on a centralized server, such as, for example, a cloud computing service.

FIG. 13 is a block diagram of a system including computing device 1600. Consistent with an embodiment of the disclosure, the aforementioned memory storage and processing unit can be implemented in a computing device, such as computing device 1600 of FIG. 13. Any suitable combination of hardware, software, or firmware can be used to implement the memory storage and processing unit. For example, the memory storage and processing unit can be implemented with computing device 1600 or any of other computing devices 1618, in combination with computing device 1600. The aforementioned system, device, and processors are examples and other systems, devices, and processors can comprise the aforementioned memory storage and processing unit, consistent with embodiments of the invention. Furthermore, computing device 1600 can comprise an operating environment for method 400 and/or 500 as described above. Method 400 and/or 500 can operate in other environments and is not limited to computing device 1600.

With reference to FIG. 13 a system consistent with an embodiment of the disclosure can include a computing device, such as computing device 1600. In a basic configuration, computing device 1600 can include at least one processing unit 1602 and a system memory 1604. Depending on the configuration and type of computing device, system memory 1604 can comprise, but is not limited to, volatile (e.g. random-access memory (RAM)), non-volatile (e.g. read-only memory (ROM)), flash memory, or any combination. System memory 1604 can include operating system 1605, one or more programming modules 1606, and can include a program data 1607. Operating system 1605, for example, can be suitable for controlling computing device 1600's operation. In one embodiment, programming modules 1606 can include platform 1620 and visual presentation generation module 1622. Furthermore, embodiments of the disclosure can be practiced in conjunction with a graphics library, other operating systems, or any other application program and is not limited to any particular application or system. This basic configuration is illustrated in FIG. 13 by those components within a dashed line 1608.

Computing device 1600 can have additional features or functionality. For example, computing device 1600 can also include additional data storage devices (removable and/or non-removable) such as, for example, magnetic disks, optical disks, or tape. Such additional storage is illustrated in FIG. 13 by a removable storage 1609 and a non-removable storage 1610. Computer storage media can include volatile and nonvolatile, removable and non-removable media implemented in any method or technology for storage of information, such as computer readable instructions, data structures, program modules, or other data. System memory 1604, removable storage 1609, and non-removable storage 1610 are all computer storage media examples (i.e., memory storage.) Computer storage media can include, but is not limited to, RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store information and which can be accessed by computing device 1600. Any such computer storage media can be part of device 1600. Computing device 1600 can also have input device(s) 1612 such as a keyboard, a mouse, a pen, a sound input device, a touch input device, etc. Output device(s) 1614 such as a display, speakers, a printer, etc. can also be included. The aforementioned devices are examples and others can be used.

Computing device 1600 can also contain a communication connection 1616 that can allow device 1600 to communicate with other computing devices 1618, such as over a network in a distributed computing environment, for example, an intranet or the Internet. Communication connection 1616 is one example of communication media. Communication media can typically be embodied by computer readable instructions, data structures, program modules, or other data in a modulated data signal, such as a carrier wave or other transport mechanism, and include any information delivery media. The term "modulated data signal" can describe a signal that has one or more characteristics set or changed in such a manner as to encode information in the signal. By way of example, and not limitation, communication media can include wired media such as a wired network or direct-wired connection, and wireless media such as acoustic, radio frequency (RF), infrared, and other wireless media. The term computer readable media as used herein can include both storage media and communication media.

As stated above, a number of program modules and data files can be stored in system memory 1604, including operating system 1605. While executing on processing unit 1602, programming modules 1606 (e.g., application 1620, visual presentation generation module 1622) can perform processes including, for example, one or more disclosed method stages as described above. The aforementioned process is an example, and processing unit 1602 can perform other processes. Other programming modules that can be used in accordance with embodiments of the present disclosure can include electronic mail and contacts applications, word processing applications, spreadsheet applications, database applications, slide presentation applications, drawing or computer-aided application programs, etc.

Generally, consistent with embodiments of the disclosure, program modules can include routines, programs, components, data structures, and other types of structures that can perform particular tasks or that can implement particular abstract data types. Moreover, embodiments of the disclosure can be practiced with other computer system configurations, including hand-held devices, multiprocessor systems, microprocessor-based or programmable consumer electronics, minicomputers, mainframe computers, and the like. Embodiments of the disclosure can also be practiced in distributed computing environments where tasks are performed by remote processing devices that are linked through a communications network. In a distributed computing environment, program modules can be located in both local and remote memory storage devices.

Furthermore, embodiments of the disclosure can be practiced in an electrical circuit comprising discrete electronic elements, packaged or integrated electronic chips containing logic gates, a circuit utilizing a microprocessor, or on a single chip containing electronic elements or microprocessors. Embodiments of the disclosure can also be practiced using other technologies capable of performing logical operations such as, for example, AND, OR, and NOT, including but not limited to mechanical, optical, fluidic, and quantum technologies. In addition, embodiments of the disclosure can be practiced within a general-purpose computer or in any other circuits or systems.

Embodiments of the disclosure, for example, can be implemented as a computer process (method), a computing system, or as an article of manufacture, such as a computer program product or computer readable media. The computer program product can be a computer storage media readable by a computer system and encoding a computer program of instructions for executing a computer process. The computer program product can also be a propagated signal on a carrier readable by a computing system and encoding a computer program of instructions for executing a computer process. Accordingly, the present disclosure can be embodied in hardware and/or in software (including firmware, resident software, micro-code, etc.). In other words, embodiments of the present disclosure can take the form of a computer program product on a computer-usable or computer-readable storage medium having computer-usable or computer-readable program code embodied in the medium for use by or in connection with an instruction execution system. A computer-usable or computer-readable medium can be any medium that can contain, store, communicate, propagate, or transport the program for use by or in connection with the instruction execution system, apparatus, or device.

The computer-usable or computer-readable medium can be, for example but not limited to, an electronic, magnetic, optical, electromagnetic, infrared, or semiconductor system, apparatus, device, or propagation medium. More specific computer-readable medium examples (a non-exhaustive list), the computer-readable medium can include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Embodiments of the present disclosure, for example, are described above with reference to block diagrams and/or operational illustrations of methods, systems, and computer program products according to embodiments of the disclosure. The functions/acts noted in the blocks can occur out of the order as shown in any flowchart. For example, two blocks shown in succession can in fact be executed substantially concurrently or the blocks can sometimes be executed in the reverse order, depending upon the functionality/acts involved.

While certain embodiments of the disclosure have been described, other embodiments can exist. Furthermore, although embodiments of the present disclosure have been described as being associated with data stored in memory and other storage mediums, data can also be stored on or read from other types of computer-readable media, such as secondary storage devices, like hard disks, floppy disks, or a CD-ROM, a carrier wave from the Internet, or other forms of RAM or ROM. Further, the disclosed methods' stages can be modified in any manner, including by reordering stages and/or inserting or deleting stages, without departing from the invention.

All rights including copyrights in the code included herein are vested in and the property of the Applicant. The Applicant retains and reserves all rights in the code included herein, and grants permission to reproduce the material only in connection with reproduction of the granted patent and for no other purpose.

The present invention and platform include at the least the following aspects:

Aspect 1: A method for generating a visual presentation of a theme, the method comprising: providing, by a system having at least one processor, a parent visual element displaying information relating to a selected [or designated] theme, the parent visual element configured to be associated with at least one attribute visual element; providing at least one attribute visual element based at least on the selected theme, the at least one attribute visual element configured to be linked with the parent visual element in a linking pattern or arrangement; modifying the parent visual element and at least one attribute visual element to display visual indicia configured to communicate information relevant to at least one of: the parent visual element, the theme, determine a relationship between at least one of: the parent visual element and at least one attribute visual element, the at least one attribute visual element and the theme, and the at least one attribute visual element and another attribute visual element; generating, by the system, based at least on a predefined visual presentation template, a visual presentation comprising the parent visual element linked with the at least one modified attribute visual element in a linking pattern; displaying, by the system, the visual presentation for interaction with a subject or user.

Aspect 2: A system for generating a visual presentation of a theme, comprising: at least one memory having computer-accessible instructions; and at least one processor functionally coupled to the at least one memory and configured by at least a portion of the computer-accessible instructions to: provide a parent visual element displaying information relating to a selected [or designated] theme, the parent visual element linked to or associated with at least one attribute visual element; provide at least one attribute visual element based at least on the selected theme, the at least one attribute visual element configured to be linked with the parent visual element in a linking pattern or arrangement; modify the at least one attribute visual element to display visual indicia configured to communicate information relevant to at least one of: the parent visual element, the theme, determine a relationship between at least one of: the parent visual element and at least one attribute visual element, the at least one attribute visual element and the theme, and the at least one attribute visual element and another attribute visual element; generate, based at least on a predefined visual presentation template, a visual presentation comprising the parent visual element linked with the modified at least one attribute visual element in a linking pattern or arrangement; and display the visual presentation for interaction with a subject or user.

Aspect 3: A method for treating memory impairment in a subject, the method comprising the step of administering an interactive visual presentation to the subject, the visual presentation comprising: a parent visual element displaying information relating to a selected theme, the parent visual element associated with at least one attribute visual element; at least one attribute visual element related to at least on the selected theme, the at least one attribute visual element configured to be linked with the parent visual element in a linking pattern or arrangement, each attribute visual element displaying visual indicia configured to communicate information relevant to at least one of: the parent visual element, the theme, determine a relationship between at least one of: the parent visual element and at least one attribute visual element, the at least one attribute visual element and the theme, and the at least one attribute visual element and another attribute visual element; wherein the parent visual element is linked with each of the attribute visual element in a linking pattern or arrangement.

Aspect 4: The method or system of any preceding aspect, further comprising sorting the at least one attribute visual element based at least on one trait associated with the at least one attribute visual element. Aspect 5: The method or system of any preceding aspect, wherein generating the visual presentation is further based on selection criteria.

Aspect 6: The method or system of any preceding aspect, further comprising a plurality of attribute visual elements. Aspect 7: The method or system of any preceding aspect, wherein the at least one attribute visual elements comprises a primary attribute visual element, a secondary attribute visual element, or a tertiary attribute visual element, or a combination thereof. Aspect 8: The method or system of any preceding aspect, wherein the linking pattern or arrangement comprises a map, chart, diagram, layout, or the like. Aspect 9: The method or system of any preceding aspect, wherein the theme relates to an event, activity, instructions, or the like. Aspect 10: The method or system of any preceding aspect, further comprising modifying at least one attribute visual element to display an image or media asset matching the indicia of the at least one attribute visual element. Aspect 11: The method or system of any preceding aspect, wherein the interaction comprises viewing the visual presentation. Aspect 12: The method or system of any preceding aspect, wherein the interaction comprises viewing the at least one attribute visual element according to the linking pattern or arrangement. Aspect 13: The method or system of any preceding aspect, wherein each of the at least one attribute visual element has an arrangement position; and wherein the interaction comprises viewing the at least one attribute visual element according to the arrangement position within the linking pattern or arrangement. Aspect 14: The method or system of any preceding aspect, wherein the interaction comprises navigating the visual presentation. Aspect 15: The method or system of any preceding aspect, wherein the interaction comprises memory training using the visual presentation. Aspect 16: The method or system of any preceding aspect, memory training comprises a predetermined number of repeated interactions or uses of the visual presentation. Aspect 17: The method or system of any preceding aspect, wherein the interaction with the visual presentation is effective to improve memory [or treat memory impairment] of the subject or user. Aspect 18: The method or system of any preceding aspect, wherein the interaction with the visual presentation is effective to improve memory [or treat memory impairment] corresponding to a selection structure or region of the subject or user brain. Aspect 19: The method or system of any preceding aspect, wherein an effectiveness to improve memory of the subject or user is determined or measured by at least one of: a behavioral assessment, imaging scan of brain structure or activity; and brain activity assessment. Aspect 20: The method or system of any preceding aspect, wherein the behavior assessment comprises at least one standardized assessment tool (e.g., Stebbins, GT, Neuropsychological Testing in Textbook of Clinical Neurology, 2007; Johns, P, Mild Cognitive Impairment in Clinical Neuroscience, 2014; Butler, c, and Zeman, A, The Neurology of Consciousness, 2016, and the like). Aspect 21: The method or system of any preceding aspect, wherein an assessment measure comprises determining an effect or impact on at least one of: behavior, memory, emotion, stress, frustration, anger, confusion, irritation, agitation, mood (e.g., depression, anxiety, etc.), withdrawal, compliance, family engagement, physical complaints, attitude, self-engagement, need for medications, hospital visits, hospital admittances, visuospatial function, global cognition, spatial memory, executive function, independence, autonomy, verbal fluency, apathy, and disinhibition. Aspect 22: The method or system of any preceding aspect, wherein the imaging scan comprises a structural or functional magnetic resonance imaging (MRI) scan. Aspect 23: The method or system of any preceding aspect, wherein the selected structure or region of the brain is at least one of: a habit region of the brain, neostriatum, striatum, globus pallidus, and the basal ganglia. Aspect 24: A method of creating profiles of a plurality of users based on user behavior, wherein the method is a computer implemented method, the method comprising: receiving at least one attribute element from a visual presentation accessed by a user of the plurality of users; retrieving content from each of the at least one attribute element of the visual presentation; analyzing content from each of the at least one attribute element of visual presentations, wherein analyzing content from a visual presentation comprises analyzing content corresponding to at least one content type present on the visual presentation; and identifying a plurality of keywords corresponding to the visual presentation based on the analyzing, wherein the plurality of keywords constitutes a profile of the user. Aspect 25: The method of any preceding aspect, wherein the plurality of keywords is associated with a plurality of prominence values, wherein the profile of the user further comprises the plurality of prominence values. Aspect 26: The method of any preceding aspect, wherein analyzing comprises performing at least one machine learning (ML) technique on content contained in the visual presentation. Aspect 27: The method of any preceding aspect, wherein analyzing comprises performing natural language processing (NLP) of content contained in the visual presentation. Aspect 28: The method of any preceding aspect, wherein analyzing comprises performing natural language processing (NLP) of textual content contained within in the visual presentation. Aspect 29: The method of any preceding aspect, wherein the visual presentation comprises textual content and non-textual content. Aspect 30: The method of any preceding aspect, wherein the non-textual content comprises at least one of audio content, an image, video content and a multimedia content. Aspect 31: The method of any preceding aspect, wherein analyzing further comprises converting the non-textual content into a textual content. Aspect 32: The method of any preceding aspect, further comprising determining an aggregated prominence value corresponding to a keyword based on a first prominence value of the keyword corresponding to a first visual presentation and a second prominence value of the keyword corresponding to a second visual presentation. Aspect 33: The method of any preceding aspect, wherein the aggregated prominence value is further based on a time decay value associated with each of the first prominence value and the second prominence value. Aspect 34: The method of any preceding aspect, further comprising predicting a first part of a first profile corresponding to a first user based on a first part of the second profile corresponding to a second user, wherein the predicting is based on a result of a comparison between a second part of the first profile and a second part of the second profile. Aspect 35: The method of any preceding aspect, wherein a profile of a user further comprises at least one characteristic of the user.

Aspect 36: The method or system of any preceding aspect, further comprising predicting a clinical status of a user or patient. Aspect 37: A computer implemented method for predicting a clinical status of a patient, the computer implemented method comprising: monitoring user behavior on a user device operated by the patient during interaction across a plurality of visual presentations having a plurality of attribute elements, each visual presentation having a plurality of user interface pages corresponding to the plurality of attribute elements for interacting with the visual presentation; analyzing the user behavior; and determining a clinical status of the patient based at least on analysis of the user behavior. Aspect 38: The method of any preceding aspect, wherein the clinical status corresponds to at least one clinical intervention. Aspect 39: The method of any preceding aspect, further comprising determining a confidence value associated with the clinical status, wherein the confidence value represents a degree of certainty of the patient's need for the at least one clinical intervention. Aspect 40: The method of any preceding aspect, wherein the clinical status corresponds to at least one of: a neuro-behavioral assessment, cognition status, emotion status, motor status, and sensation status. Aspect 41: The method of any preceding aspect, wherein monitoring comprises extracting user behavior data captured during user interaction with the plurality of visual presentations. Aspect 42: The method of any preceding aspect, wherein monitoring further comprises extracting biometric data associated with the user, and wherein determining clinical status of the patient is based at least on analysis of user behavior data and biometric data. Aspect 43: The method of any preceding aspect, wherein monitoring comprises extracting at least one key element from at least one user page corresponding to a visual presentation accessed by the patient. Aspect 44: The method of any preceding aspect, wherein the monitoring comprises extracting content from the plurality of visual presentations, and wherein the analyzing comprises performing machine learning techniques on the content. Aspect 45: The method of any preceding aspect, wherein the machine learning techniques comprises at least one of a supervised machine learning and an unsupervised machine learning. Aspect 46: The method of any preceding aspect, wherein the user behavior comprises at least one of visiting the plurality of visual presentations, interacting with the plurality of visual presentations, and the like. Aspect 47: The method of any preceding aspect, wherein user behavior data comprises time series data and success rate data.

Aspect 48: The method of any preceding aspect, wherein time series data comprises duration required for the user to navigate through all user interface pages within a visual presentation, time interval between navigating each user interface page within a visual presentation between, time viewing a prompt prior to making a choice during interaction, frequency of accessing a user interface pages within a visual presentation, sequence of accessing user interface pages within a visual presentation, duration viewing off target, frequency viewing off target, and the like. Aspect 49: The method of any preceding aspect, wherein success rate data comprises percentage of time where the user successfully completes a visual presentation corresponding to a task. Aspect 50: The method of any preceding aspect, wherein the user behavior data comprises data associated with the user physical interaction with the user device such as: strength of screen press, dwell time of finger on screen, navigation strategies, and typing errors, accelerometer data during user interaction, and the like. Aspect 51: The method of any preceding aspect, wherein biometric data comprises ocular measures such as pupillary size and reflex, eye movement, facial expression, accelerometry data, actigraphy data, quantitative and qualitative measures of sleep, heart rate, instantaneous beat-to-beat heart rate variability, sleep disturbances, changes in sleep architecture, single lead EKG data, pulse oximetry data, GPS location data, multi-lead EKG data, blood pressure data, capnography data (e.g., respiratory gases, like CO2, etc.), walking speed variability, pace, left/right leg symmetry, step time, stance time, step length, swing time, stance time, step velocity, step length asymmetry, step time asymmetry, and the like.

Aspect 52: The method of any preceding aspect, further comprising employing a tracker on the user device operated by the patient, and wherein the monitoring is performed by the tracker. Aspect 53: The method of any preceding aspect, wherein each of the plurality of visual presentations comprises a tracker configured to perform the monitoring. Aspect 54: The method of any preceding aspect, further comprising: parsing content of at least one visual presentations of the plurality of visual presentations; and identifying at least one theme based on the parsing. Aspect 55: The method of any preceding aspect, further comprising extracting a reference set of key elements associated with at least one theme based on the parsing. Aspect 56: The method of any preceding aspect, further comprising: identifying the patient based on at least one unique identifier associated with the request; administering a visual presentation of the plurality of visual presentations to the patient on a user device operated by the patient; and extracting a set of key elements from the visual presentation, wherein analyzing comprises analyzing the set of key elements, wherein determining the clinical status of the patient is based on analyzing the set of key elements. Aspect 57: The method of any preceding aspect, wherein analyzing the set of key elements comprises comparing the set of key elements with a reference set of key elements associated with the visual presentation, wherein the reference set of key elements represents at least one offered by the visual presentation. Aspect 58: The method of any preceding aspect, further comprising: receiving a request to access a visual presentation by a user device operated by the patient; identifying the patient based on at least one unique identifier associated with the request; retrieving the clinical status associated with the patient; and transmitting at least one query to the user device based on the clinical status. Aspect 59: The method of any preceding aspect, wherein the query comprises a neurobehavioral assessment associated with cognition, emotion, motor, and sensation; a cognition test associated with drawing tasks, memory tasks, and executive function tasks; or the like; and wherein analyzing comprises analyzing the neurobehavioral assessment data and cognition test data from the user query, and wherein determining the clinical status of the patient is based at least on analyzing the neurobehavioral assessment data and cognition test data from the user query.

Aspect 60: The method of any preceding aspect, further comprising updating a patient database with the clinical status of the patient. Aspect 61: The method or system of any preceding aspect, wherein memory includes at least one of: spatial, temporal, spatial-temporal, working and short-term memory. Aspect 62: The method or system of any preceding aspect, improving memory or treating memory impairment comprises preventing a memory-related disease or disorder. Aspect 63: The method or system of any preceding aspect, wherein memory impairment comprises a memory-related disorder or disease.

Aspect 64: The method or system of any preceding aspect, wherein the memory-related disease or disorder is associated with age-related memory impairment or loss of brain function. Aspect 65: The method or system of any preceding aspect, wherein the memory-related disease or disorder comprises a degenerative disease or a function-decreasing disorder. Aspect 66: The method or system of any preceding aspect, wherein the memory-related related disease or disorder is selected from Alzheimer's, Parkinson's, Vascular dementia, Mixed dementia, Frontotemporal dementia, Huntington's disease, Chronic Traumatic Encephalopathy (CTE); mental health disorders, including schizophrenia, mood disorders, including depression and anxiety; and function decreasing disorders or conditions, including declines due to age, or other so-called "benign changes with aging", e.g., poorer memory, cognitive decline, that have no specific neurodegenerative or biological bases.

Aspect 67: The method for treating of any preceding aspect, further comprising the step of identifying a subject in need of treatment for memory impairment. Aspect 68: The method or system of any preceding aspect, wherein the subject has been diagnosed with a need for memory impairment treatment prior to the administering step. Aspect 69: The method or system of any preceding aspect, wherein the subject has been diagnosed with a memory-related disease or disorder associated with age-related memory loss or loss of brain function.

Aspect 70: The method or system of any preceding aspect, wherein the subject is a mammal.

Aspect 71: The method or system of any preceding aspect, wherein the mammal is a human.

Aspect 72: The method or system of any preceding aspect, wherein an effective amount or effective to is a therapeutically effective amount. Aspect 73: The method or system of any preceding aspect, wherein the effective amount or effective to is a prophylactically effective amount. Aspect 74: The method or system of any preceding aspect, further comprising the step of identifying a subject in need of memory training or memory impairment treatment.

Aspect 75: The method or system of any preceding aspect, wherein the subject in need of anti-aging treatment comprises having at least one risk factor for developing a memory-related disease or disorder. Aspect 76: The method or system of any preceding aspect, further comprising diagnosing the subject as having a memory-related disorder or disease.

Aspect 77: The method or system of any preceding aspect, wherein diagnosing comprises performing a physical examination upon the subject and making a finding. Aspect 78: The method or system of any preceding aspect, wherein diagnosing comprises performing an assessment upon the subject and making a finding. Aspect 79: The method or system of any preceding aspect, wherein the finding comprises identifying at least one risk factor for developing a memory-related disease or disorder. Aspect 80: The method or system of any preceding aspect, wherein diagnosing comprises performing an experiment upon the subject and identifying a level of a biological marker. Aspect 81: The method or system of any preceding aspect, wherein the biological marker is a marker for a memory-related disease or disorder. Aspect 82: The method or system of any preceding aspect, where in the biological marker is determined using a biological sample from the subject. Aspect 83: The method or system of any preceding aspect, where in the biological sample is selected from a cell, blood, saliva, urine, tissue, or phlegm. Aspect 84: A system comprising a memory storage and a processing unit coupled to the memory storage, wherein the processing unit is operative to perform the method of any preceding aspect. Aspect 85: A computer-readable medium comprising a set of instructions which, when executed, perform a method of any preceding aspect.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way appreciably intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications may be referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein can be different from the actual publication dates, which can require independent confirmation. The patentable scope of the invention is defined by the claims, and can include other examples that occur to those skilled in the art. Such other examples are intended to be within the scope of the claims if they have structural elements that do not differ from the literal language of the claims, or if they include equivalent structural elements with insubstantial differences from the literal languages of the claims. Insofar as the description above and the accompanying drawings disclose any additional subject matter that is not within the scope of the claims below, the disclosures are not dedicated to the public, and the right to file one or more applications to claims relating to such additional disclosures is reserved.

What is claimed:

1. A method for administering an interactive visual presentation to a user for treating a memory-related disease or disorder, the method comprising:

providing, by a system having at least one processor, a parent visual element displaying information relating to a selected theme, the parent visual element configured to be associated with at least one attribute visual element;

providing at least one attribute visual element based at least on the selected theme, the at least one attribute visual element configured to be linked with the parent visual element in a linking pattern;

modifying the parent visual element and at least one attribute visual element to display content configured to communicate information relevant to at least one of: the parent visual element and the theme, determine a relationship between at least one of: the parent visual element and at least one attribute visual element, the at least one attribute visual element and the theme, and the at least one attribute visual element and another attribute visual element;

generating, by the system, based at least on a predefined visual presentation template, a visual presentation comprising the parent visual element linked with the at least one modified attribute visual element in a linking pattern;

administering, by the system, the visual presentation to a user for interaction; wherein the interaction with the visual presentation is effective to treat a memory-related disease or disorder of the user; and creating a user profile of the user based on user behavior, wherein creating a user profile comprises:
receiving at least one attribute element from a visual presentation accessed by the user;
retrieving content from each of the at least one attribute visual element of the visual presentation;
analyzing content from each of the at least one attribute visual element of visual presentations, wherein analyzing content comprises analyzing content corresponding to at least one content type present in the each of the at least one attribute visual element of the visual presentation; and identifying a plurality of keywords corresponding to the visual presentation based on the analyzing, wherein the plurality of keywords constitutes a profile of the user; wherein the plurality of keywords is associated with a plurality of prominence values; and wherein the profile of the user further comprises the plurality of prominence values;

wherein an effectiveness to treat is determined based on improvement of at least one of: an assessment measure, imaging scan of brain structure or activity, and brain activity assessment; and wherein the assessment measure comprises a measure of at least one of: behavior, cognition, memory, emotion, stress, frustration, anger, confusion, irritation, agitation, mood, withdrawal, compliance, family engagement, physical complaints, attitude, self-engagement, need for medications, hospital visits, hospital admittances, visuospatial function, global cognition, spatial memory, executive function, independence, autonomy, verbal fluency, apathy, and disinhibition.

2. The method of claim 1, wherein analyzing comprises performing at least one machine learning (ML) technique on content contained in the visual presentation.

3. The method or claim 2, further comprising predicting a clinical status of the user, wherein predicting a clinical status of the user comprises:
monitoring user behavior on a user device operated by the user during interaction across a plurality of visual presentations;
analyzing the user behavior; and
determining a clinical status of the patient based at least on analysis of the user behavior.

4. The method of claim 3, further comprising determining a confidence value associated with the clinical status, wherein the confidence value represents a degree of certainty of the user's need for at least one clinical intervention.

5. The method of claim 4, wherein monitoring comprises extracting user behavior data captured during user interaction with the plurality of visual presentations, and extracting biometric data associated with the user, and wherein determining clinical status of the patient is based at least on analysis of user behavior data and biometric data.

6. The method of claim 5, wherein the machine learning techniques comprises at least one of a supervised machine learning or an unsupervised machine learning.

7. The method of claim 6, wherein the user behavior data comprises data associated with the user physical interaction with the user device selected from one or more of: strength of screen press, dwell time of finger on screen, navigation strategy, typing errors, and accelerometer data during user interaction.

8. The method of claim 7, wherein biometric data comprises at least one of: ocular measures, pupillary size and reflex, eye movement, facial expression, accelerometry data, actigraphy data, quantitative and qualitative measures of sleep, heart rate, instantaneous beat-to-beat heart rate variability, sleep disturbances, changes in sleep architecture, single lead EKG data, pulse oximetry data, GPS location data, multi-lead EKG data, blood pressure data, capnography data, walking speed variability, pace, left/right leg symmetry, step time, stance time, step length, swing time, stance time, step velocity, step length asymmetry, and step time asymmetry.

9. The method of claim 8, further comprising:
a) receiving a request to access a visual presentation by a user device operated by the user;
b) identifying the user based on at least one unique identifier associated with the request;
c) retrieving the clinical status associated with the user; and
d) transmitting at least one query to the user device based at least on the clinical status and user behavior data.

10. The method of claim 9, wherein the query comprises a neurobehavioral assessment associated with cognition, emotion, motor, and sensation; a cognition test associated with drawing tasks, memory tasks, and executive function tasks; and wherein analyzing comprises analyzing the neurobehavioral assessment data and cognition test data from the user query, and wherein determining the clinical status of the patient is based at least on analyzing the neurobehavioral assessment data and cognition test data from the user query.

11. The method of claim 10, wherein the query comprises a neurobehavioral assessment associated with cognition, emotion, motor, and sensation; a cognition test associated with drawing tasks, memory tasks, and executive function tasks; and wherein analyzing comprises analyzing the neurobehavioral assessment data and cognition test data from the user query, and wherein determining the clinical status of the patient is based at least on analyzing the neurobehavioral assessment data and cognition test data from the user query.

12. The method of claim 11, further comprising the step of identifying the user as in need of memory impairment treatment.

13. The method of claim 12, further comprising diagnosing the user as having a memory-related disorder or disease.

14. The method of claim 13, wherein the memory-related disease or disorder is selected from Alzheimer's Disease, Parkinson's Disease, Vascular dementia, Mixed dementia, Frontotemporal dementia, Huntington's disease, Chronic Traumatic Encephalopathy (CTE), mental health disorders, schizophrenia, mood disorders, depression and anxiety; function decreasing disorders, and cognitive decline.

15. A system for treating a user having a memory-related disease or disorder, comprising:
at least one memory having computer-accessible instructions; and
at least one processor functionally coupled to the at least one memory and configured by at least a portion of the computer-accessible instructions to:
provide a parent element displaying information relating to a designated theme, the parent visual element associated with at least one attribute element;
provide a plurality of attribute element based at least on the selected theme, the plurality of attribute elements configured to be linked with the parent visual element in a linking pattern;
modify the plurality of attribute elements to display content configured to communicate information relevant to at least one of: the parent element, the theme, determine a relationship between at least one of: the parent element and at least one attribute element, at least one attribute element and the theme, and at least one attribute element and another attribute element;
generate, based at least on a predefined visual presentation template and at least one neurobehavioral assessment of the user, a visual presentation comprising the parent element linked with the modified plurality of attribute elements in a linking pattern;

administering the visual presentation for interaction by the user having a memory-related disease or disorder; and creating a user profile of the user based on user interaction behavior; wherein the interaction with the visual presentation is effective to treat memory impairment corresponding to a selected structure or region of the user brain selected from at least one of: a habit region of the brain, neostriatum, striatum, globus pallidus, and the basal ganglia;

wherein creating a user profile comprises:
- receiving the plurality of attribute elements from a visual presentation interacted with by the user;
- retrieving content from each of the plurality of attribute elements of the visual presentation;
- analyzing, using at least one machine learning (ML) technique, content from each of the attribute elements of visual presentations, wherein analyzing content comprises analyzing content corresponding to at least one content type present in the each of the attribute elements of the visual presentation; and
- identifying a plurality of keywords corresponding to the visual presentation based on the analyzing; wherein the plurality of keywords constitutes a profile of the user: wherein the plurality of keywords is associated with a plurality of relevance values; and wherein the profile of the user further comprises the plurality of relevance values.

16. The system of claim 15, wherein
the system is further configured to predict a clinical status of the user,
wherein predicting a clinical status of the user comprises:
monitoring user behavior on a user device operated by the user during interaction across a plurality of visual presentations having a plurality of attribute elements, each visual presentation having a user interface page corresponding to each of the plurality of attribute elements for interacting with the visual presentation;
analyzing the user behavior;
determining a clinical status of the patient based at least on analysis of the user behavior; and
determining a confidence value associated with the clinical status; wherein the clinical status corresponds to at least one clinical intervention.

17. The system of claim 16, wherein the clinical intervention comprises administering at least one query to the user device based on the clinical status; wherein the query comprises at least one of: a neurobehavioral assessment associated with one or more of cognition, emotion, motor, and sensation; or a cognition test associated with one or more of: drawing tasks, memory tasks, and executive function tasks.

18. The system of claim 17, wherein determining clinical status of the patient is based at least on one or more of neurobehavioral assessment data and cognition test data from the query.

19. The system of claim 15, wherein the system is further configured to predict a clinical status of the user based on user behavior data captured during user interaction with the system.

20. The system of claim 19, wherein user behavior data comprises data associated with the user physical interaction with the user device selected from one or more of: strength of screen press, dwell time of finger on screen, navigation strategy, typing errors, or accelerometer data during user interaction, and combinations thereof.

* * * * *